United States Patent [19]
Kaas et al.

[11] Patent Number: 5,856,314
[45] Date of Patent: Jan. 5, 1999

[54] THIO-SUBSTITUTED, NITROGEN-CONTAINING, HETEROCYCLIC PHOSPHONATE COMPOUNDS, PHARMACEUTICAL COMPOSITIONS, AND METHODS OF TREATING ABNORMAL CALCIUM AND PHOSPHATE METABOLISM

[75] Inventors: Susan Mary Kaas, Norwich, N.Y.; Frank Hallock Ebetino, Cincinnati; Marion David Francis, Cincinnati, both of Ohio

[73] Assignee: The Procter & Gamble Company, Cincinnati, Ohio

[21] Appl. No.: 240,303

[22] Filed: May 9, 1994

Related U.S. Application Data

[63] Continuation of Ser. No. 891,490, May 29, 1992, abandoned.

[51] Int. Cl.[6] .............. A61K 31/675; A61K 31/67; A61K 31/665
[52] U.S. Cl. .............. 514/89; 514/86; 514/91; 514/92; 514/94; 514/95; 514/99; 549/6; 549/218; 548/119; 548/413; 546/22; 544/243
[58] Field of Search .............. 546/22; 544/243; 514/86, 89, 91, 92, 94, 95, 99; 548/112; 549/6, 218

[56] References Cited

U.S. PATENT DOCUMENTS

| | | | |
|---|---|---|---|
| 4,208,401 | 6/1980 | Bauman | 424/54 |
| 4,267,108 | 5/1981 | Blum et al. | 260/326.61 |
| 4,325,948 | 4/1982 | Maurer et al. | 514/86 |
| 4,407,761 | 10/1983 | Blum et al. | 260/502.5 C |
| 4,588,711 | 5/1986 | Reifschneider et al. | 514/86 |
| 4,687,768 | 8/1987 | Benedict et al. | 514/102 |
| 4,746,654 | 5/1988 | Breliere et al. | 514/108 |
| 4,784,993 | 11/1988 | Bosies et al. | 514/93 |
| 4,868,164 | 9/1989 | Ebetino et al. | 514/80 |
| 4,876,247 | 10/1989 | Barbier et al. | 514/89 |
| 4,922,007 | 5/1990 | Kieczykowksi et al. | 562/13 |
| 4,933,472 | 6/1990 | Isomura et al. | 549/218 |
| 4,939,130 | 7/1990 | Jaeggi et al. | 514/94 |
| 4,939,131 | 7/1990 | Benedict et al. | 514/102 |
| 4,971,958 | 11/1990 | Bosies et al. | 514/89 |
| 5,071,840 | 12/1991 | Ebetino et al. | 514/89 |
| 5,104,863 | 4/1992 | Benedict et al. | 514/80 |
| 5,137,880 | 8/1992 | Ebetino et al. | 514/80 |

FOREIGN PATENT DOCUMENTS

| | | |
|---|---|---|
| A-26738/88 | 6/1989 | Australia . |
| A-45467/89 | 5/1990 | Australia . |
| 0100718 | 2/1984 | European Pat. Off. . |
| 0170228 | 2/1986 | European Pat. Off. . |
| 0186405 | 7/1986 | European Pat. Off. 514/86 |
| 186405 | 7/1986 | European Pat. Off. . |
| 0298553 | 1/1989 | European Pat. Off. . |
| 2835492 | 2/1980 | Germany 514/86 |
| 4011777 | 10/1990 | Germany . |
| WO 90/12017 | 10/1990 | WIPO . |
| WO 91/10646 | 7/1991 | WIPO . |

*Primary Examiner*—Amelia Owens
*Attorney, Agent, or Firm*—Karen F. Clark; William J. Winter; Richard A. Hake

[57] ABSTRACT

The present invention relates to thio-substituted, nitrogen-containing heterocyclic phosphonate compounds, including bisphosphonates, phosphonoalkylphosphinates, phosphonocarboxylates, and phosphonosulfonates, and the pharmaceutically-acceptable salts and esters thereof useful for the treatment and prevention of osteoporosis and arthritis. These compounds have the general structure:

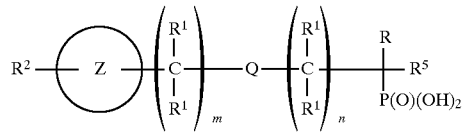

(a) Z is a monocyclic or polycyclic heterocyclic ring moiety containing one or more heteroatoms selected from O, S, or N, at least one of which is N;

(b) Q is covalent bond; O, S, N, or $NR_1$;

(c) R is COOH, $SO_3H$, $PO_3H_2$, or $P(O)(OH)R^4$, wherein $R^4$ is substituted or unsubstituted $C_1$–$C_8$ alkyl;

(d) each R1 is independently selected from —$SR^6$; —$R^8SR^6$; nil; hydrogen; unsubstituted or substituted $C_1$–$C_8$ alkyl; unsubstituted or substituted aryl; hydroxy; —$CO_2R^3$; —$O_2CR^3$; —$NR^3{}_2$; —$OR^3$; —$C(O)N(R^3)_2$; —$N(R^3)C(O)R^3$; substituted or unsubstituted benzyl; nitro; or combinations thereof;

(e) $R^2$ is one or more substituents on atoms in the Z moiety and is independently selected from —$SR^6$ and —$R^8SR^6$; where $R^6$ is H; —$CO_2R^3$; —$O_2CR^3$; —$NR^3{}_2$; —$N(R)^3C(O)R^3$; and nil; hydrogen; unsubstituted or substituted $C_1$–$C_8$ alkyl; unsubstituted or substituted aryl; hydroxy; substituted or unsubstituted benzyl; nitro; or combinations thereof;

(f) each $R^3$ is independently selected from hydrogen; substituted or unsubstituted $C_1$–$C_8$ alkyl; or $R^8SR^6$;

(g) $R^5$ is selected from —$SR^6$; $R^8SR^6$, hydrogen; hydroxy; amino; halogen; unsubstituted or substituted $C_1$–$C_8$ alkyl; and (h) $R^6$ is independently selected from H; —$C(O)R^7$; $C(S)R^7$; $C(O)NR^7{}_2$; $C(S)NR^7{}_2$; $C(O)(OR^7)$; and $C(S)(OR^7)$; wherein $R^7$ is hydrogen; or unsubstituted or substituted $C_1$–$C_8$ alkyl;

(i) $R^8$ is a substituted or unsubstituted $C_1$–$C_8$ alkyl; and at least one of $R^1$, $R^2$, $R^3$ or $R^5$ must be $SR^6$ or $R^8SR^6$.

30 Claims, No Drawings

THIO-SUBSTITUTED, NITROGEN-CONTAINING, HETEROCYCLIC PHOSPHONATE COMPOUNDS, PHARMACEUTICAL COMPOSITIONS, AND METHODS OF TREATING ABNORMAL CALCIUM AND PHOSPHATE METABOLISM

This is a continuation of application Ser. No. 07/891,490, filed on May 29, 1992 now ABN.

BACKGROUND OF INVENTION

This invention relates to novel nitrogen-containing, thio-substituted, heterocyclic phosphonate compounds, including bisphosphonates, phosphonoalkylphosphinates, phosphonocarboxylates, and phosphonosulfonates. This invention further relates to pharmaceutical compositions containing these novel compounds, as well as to a method of treating or preventing certain metabolic bone disorders characterized by abnormal calcium and phosphate metabolism, utilizing a compound or pharmaceutical composition of the present invention. Specifically, this invention relates to a method of treating or preventing osteoporosis and arthritis, especially rheumatoid arthritis and osteoarthritis, by utilizing a compound or pharmaceutical composition of the present invention.

A number of pathological conditions which can afflict warm-blooded animals involves abnormal calcium and phosphate metabolism. Such conditions may be divided into two broad categories.

1. Conditions which are characterized by anomalous mobilization of calcium and phosphate leading to general or specific bone loss, such as osteoporosis and Paget's disease,or excessively high calcium in the fluids of the body; such as hypercalcemia of tumor origin. Such conditions are sometimes referred to herein as pathological hard tissue demineralizations.

2. Conditions which cause or result from deposition of calcium and phosphate anomalously in the body, such as rheumatoid arthritis and osteoarthritis. These conditions are sometimes referred to herein as pathological calcifications.

The first category included the most common metabolic bone disorder, osteoporosis; osteoporosis is a condition in which bone hard tissue is lost disproportionately to the development of new hard tissue. Osteoporosis can be generally defined as the reduction in the quantity of bone, or the atrophy of skeletal tissue. Marrow and bone spaces become larger, fibrous binding decreases, and compact bone becomes fragile. Osteoporosis can be subclassified as menopausal, senile, drug-induced (e.g. adrenocorticoid, as can occur in steroid therapy); disease-induced (arthritic and tumor), etc.; however, the manifestations are essentially the same. In general, there are two types of osteoporosis: primary and secondary. "Secondary osteoporosis" is the result of a separate identifiable disease process or agent. However, approximately 90% of all osteoporosis cases are "primary osteoporosis". Such primary osteoporosis includes postmenopausal osteoporosis, disuse osteoporosis, age-associated osteoporosis (affecting a majority of individuals over the age of 70 to 80), and idiopathic osteoporosis, affecting middle-aged and younger men and women.

For some osteoporotic individuals, the loss of bone tissue is sufficiently great so as to cause mechanical failure of the bone structure. Bone fractures often occur, for example, in the hip and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone. This remodeling involves the erosion and filling of discrete sites on the surface of bones, by an organized group of cells called "basic multicellular units" or "BMUs". BMUs primarily consist of "osteoclasts", "osteoblasts", and their cellular precursors. In the remodeling cycle, bone is resorbed at the site of an "activated" BMU by an osteoclast, forming a resorption cavity. This cavity is then filled with bone by an osteoblast.

Normally, in adults, the remodeling cycle results in a small deficit in bone, due to incomplete filling of the resorption cavity. Thus, even in healthy adults, age-related bone loss occurs. However, in osteoporotics, there may be an increase in the number of BMUs that are activated. This increased activation accelerates bone remodeling, resulting in abnormally high bone loss.

Although its etiology is not fully understood, there are many risk factors thought to be associated with osteoporosis. These include low body weight, low calcium intake, physical inactivity, and estrogen deficiency.

Current osteoporosis treatment largely consists of calcium and estrogen administration.

The second category, involving conditions manifested by anomalous calcium and phosphate deposition, includes myositis ossificans progressive, calcinosis universalis, and such afflictions as arthritis (including, for example, rheumatoid arthritis and osteoarthritis), neuritis, bursitis, tendonitis, and other conditions which predispose involved tissue to deposition of calcium.

In addition to osteoporosis, bone loss can result from rheumatoid arthritis and osteoarthritis. Rheumatoid arthritis is a chronic, systemic and articular inflammatory disorder characterized by weakening of the joint capsules and ligaments, followed by destruction of cartilage, ligaments, tendon and bone, and a decrease in viscosity and other alterations in the synovial fluid. Rheumatoid arthritis symptoms include systemic weakness, fatigue, localized pain, stiffness and weakness and swelling and deformation of the joints of the body. Rheumatoid arthritis is most common in women in the fourth to sixth decade of life.

The pathogenesis of rheumatoid arthritis, leading to the destruction of the joints, is characterized by two phases: 1) an exudative phase involving the microcirculation and the synovial cells that allow an influx of plasma proteins and cellular elements into the joint and 2) a chronic inflammatory phase occurring in the sub-synovium characterized by pannus (granulation tissue) formation in the joint and sub-chondral bone, space, bone erosion, and cartilage destruction. The pannus may form adhesions and scar tissue which causes the joint deformities characteristic of rheumatoid arthritis.

The etiology of rheumatoid arthritis remains obscure. Infectious agents such as bacteria and viruses have been implicated. A current hypothesis is that the Epstein-Barr (EBV) virus is a causative agent for rheumatoid arthritis.

Current rheumatoid arthritis treatment consists predominantly of symptomatic relief by administration of non-steroidal anti-inflammatory drugs. Non-steroidal anti-inflammatory drug treatment is mainly effective in the early stages of rheumatoid arthritis; it is unlikely it will produce suppression of joint inflammation if the disease is present for more than one year. Gold, methotrexate, immunosuppressants and corticosteroids have been tried with limited success.

On the other hand, osteoarthritis is an inherently non-inflammatory disorder of the movable joints characterized by deterioration and abrasion of articular cartilage, as well as by formation of new bone at the joint surface. As osteoarthritis progresses, the surface of the articular cartilage is disrupted and wear particles gain access to the synovial fluid which in turn stimulates phagocytosis by macrophage cells. Thus, an inflammatory response is eventually induced in osteoarthritis. Common clinical symptoms of osteoarthritis include cartilaginous and bony enlargements of the finger joints and stiffness on awakening, and pain from movement.

Common symptomatic treatments for osteoarthritis include analgesics, anti-inflammatories, steroids, and physical therapy.

A variety of phosphonic acid derivatives have been proposed for use in the treatment and prophylaxis of diseases involving abnormal calcium and phosphate metabolism. For example, numerous references, all incorporated by reference herein, disclose compositions containing polyphosphonates, in particular bisphosphonates such as ethane-1-hydroxy-1, 1-diphosphonic acid ("EHDP"), and their use in inhibiting anomalous deposition and mobilization of calcium and phosphate in animal tissue: U.S. Pat. No. 3,683,080, issued Aug. 8, 1972 and U.S. Pat. No. 4,230,700, issued Oct. 28, 1980, both to Francis, and U.S. Pat. No. 4,868,164 to Ebetino, issued Sep. 19, 1989. Numerous other references describe heterocyclic-substituted diphosphonic acids useful for the treatment of osteoporosis and/or arthritis, and are hereby incorporated by reference herein: U.S. Pat. No. 4,868,164, to Ebetino, et al., issued Sep. 19, 1989; U.S. Pat. No. 5,104,863, to Benedict, et al., issued Apr. 14, 1992; U.S. Pat. No. 4,267,108, to Blum et al., issued May 12, 1981; European Patent Application Publication of Boehringer Mannhein GmbH No. 170,228, published Feb. 5, 1986; European Patent Application Publication No. 186,405, of Benedict and Perkins, published Jul. 2, 1986; U.S. Pat. No. 4,754,993, Bosies, et al. issued Nov. 15, 1988; U.S. Pat. No. 4,939,130, Jaeggi, et al., issued Jul. 3, 1990; U.S. Pat. No. 4,971,958, Bosies, et al. issued Nov. 20, 1990; DE 40 11 777, Jaeggi, K., published Oct. 18, 1990; WO 90/12017, of Dunn, et al., published Oct. 18, 1990; WO 91/10646, Youssefyeh, R., et al., published Jul. 25, 1991; AU-A-26738/88, Jaeggi, published Jun. 15, 1989, AU-A-45467/89 (assigned to Ciba-Geigy), published May 31, 1990; and U.S. Pat. No. 4,208,401 to Bauman issued Jun. 17, 1980.

In addition, several references describe sulfur-containing phosphonic acids which are said to be useful in the treatment of inflammation symptoms, See e.g. U.S. Pat. No. 4,746,654 to Breliere et al. (assigned to Sanofi), issue May 24, 1988; U.S. Pat. No. 4,876,247 to Barbier et al., issued Oct. 24, 1989; and EPO 100,718 to Breliere et al. (assigned to Sanofi), published Feb. 15, 1984. Also, U.S. Pat. No. 5,071,840 to Ebetino et al., issued Dec. 10, 1991, discloses sulfur-containing heterocycle-substituted diphosphonates in which the diphosphonate-substituted carbon moiety is attached to a carbon atom in a nitrogen-containing six-membered ring heterocycle. The compounds described therein are useful in the treatment of conditions involving abnormal calcium and phosphate metabolism, specifically osteoporosis and arthritis.

Further, European Pat. No. 0,298,553 to Ebetino, published Jan. 11, 1989 describes thiol-substituents amongst a myriad of other substituents, for suitable as substituents on methylene phosphonoalkylphosphinic acids. There is no teaching therein, however, that a thiol substituent increases anti-resorptive and antiarthritis activity over the numerous other substituents disclosed.

None of these references, however, disclose the utility of a thio-substituted, nitrogen-containing heterocyclic bisphosphonates, phosphonocarboxylates and phosphonosulfonates in preventing and treating osteoporosis and rheumatoid arthritis and osteoarthritis. The thio-substituents defined herein include thiol, alkyl thiols, thioesters, alkyl thioesters, dithioesters and alkyl dithioesters, thiocarbamates, alkyl thiocarbamates, dithiocarbamates, alkyl dithiocarbamates, thiocarbonates, alkyl thiocarbonates, dithiocarbonate, and alkyl dithiocarbonates. Further, the compounds of the present invention have osteoprotective activity of joint destruction in arthritic conditions and have that activity as an additional benefit in the treatment of arthritis over the above merely relieving the symptoms of inflammation. The term "osteoprotective activity" as used herein means disease-modifying activity on bone and surrounding soft issue at the site.

It has been surprisingly discovered that the compounds of the present invention have more potent bone antiresorptive activity, and also greater therapeutic utility in treating osteoporosis and arthritis, than heterocyclic bisphosphonate compounds not having a thio-substituent.

It is therefore an object of the present invention to provide new more potent, compounds which are potent bone resorption inhibiting agents useful in osteoporosis therapy and anti-arthritic agents useful in the treatment of osteoarthritis and rheumatoid arthritis. It is a further object of the present invention to provide pharmaceutical compositions useful for the treatment and prophylaxis of abnormal calcium and phosphate metabolism and for the treatment and prophylaxis of arthritis, especially rheumatoid arthritis and osteoarthritis. In addition, it is an object of the present invention to provide methods for treating or preventing diseases characterized by abnormal calcium and phosphate metabolism in humans or other mammals, including osteoporosis, and arthritis, especially rheumatoid arthritis and osteoarthritis.

These and other objects of the present invention will become apparent from the detailed disclosure of the present invention provided hereinafter.

SUMMARY OF THE INVENTION

The present invention relates to thio-substituted, nitrogen-containing heterocyclic phosphonate compounds, including bisphosphonates, phosphonoalkylphosphonates, phosphonocarboxylates, and phosphonosulfonates, and the pharmaceutically-acceptable salts and esters thereof. The present invention further relates to pharmaceutical compositions containing a safe and effective amount of a compound of the present invention, and pharmaceutically-acceptable excipients. Finally, the present invention relates to methods for treating or preventing pathological conditions characterized by abnormal calcium and phosphate metabolism in humans or other mammals, including treating or preventing osteoporosis and arthritis, especially rheumatoid arthritis and osteoarthritis. This method comprises administering to a human or other mammal in need of such treatment of a safe and effective amount of a compound or composition of the present invention. These compounds have the general structure:

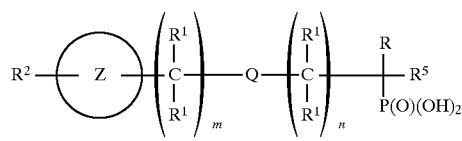

(a) Z is a monocyclic or polycyclic heterocyclic ring moiety containing one or more heteroatoms selected from O, S, or N, at least one of which is N;

(b) Q is covalent bond; 0, S, N, or $NR^1$;
(c) R is COOH, $SO_3H$, $PO_3H_2$, or $P(O)(OH)R^4$, wherein $R^4$ is substituted or unsubstituted $C_1$–$C_8$ alkyl;
(d) each R1 is independently selected from —$SR^6$; —$R^8SR^6$; nil; hydrogen; unsubstituted or substituted $C_1$–$C_8$ alkyl; unsubstituted or substituted aryl; hydroxy; —$CO_2R^3$; —$O_2CR^3$; —$NR^3_2$; —$OR^3$; —$C(O)N(R^3)_2$; —$N(R^3)C(O)R^3$; substituted or unsubstituted benzyl; nitro; or combinations thereof;
(e) $R^2$ is one or more substituents on atoms in the Z moiety and is independently selected from —$SR^6$ and —$R^8SR^6$; where $R^6$ is H; —$CO_2R^3$; —$O_2CR^3$; —$NR^3_2$; —$N(R)^3C(O)R^3$; and nil; hydrogen; unsubstituted or substituted $C_1$–$C_8$ alkyl; unsubstituted or substituted aryl; hydroxy; substituted or unsubstituted benzyl; nitro; or combinations thereof;
(f) each $R^3$ is independently selected from hydrogen; substituted or unsubstituted $C_1$–$C_8$ alkyl; or $R^8SR^6$;
(g) $R^5$ is selected from —$SR^6$, $R^8SR^6$, hydrogen; hydroxy; amino; halogen; unsubstituted or substituted $C_1$–$C_8$ alkyl; and
(h) $R^6$ is independently selected from H; —$C(O)R^7$; $C(S)R^7$; $C(O)NR^7_2$; $C(S)NR^7_2$; $C(O)(OR^7)$; and $C(S)(OR^7)$; wherein $R^7$ is hydrogen; or unsubstituted or substituted $C_1$–$C_8$ alkyl;
(i) $R^8$ is a substituted or unsubstituted $C_1$–$C_8$ alkyl; and at least one of $R^1$, $R^2$, $R^3$ or $R^5$ must be $SR^6$ or $R^8SR^6$.

In this general structure, Z is a nitrogen-containing, monocyclic or polycyclic, saturated or unsaturated heterocyclic ring moiety. In addition, m and n and m+n are integers from about 0 to about 10 (preferably m+n=0, 1 or 2); and Q is a covalent bond or a moiety selected from the group consisting of oxygen, nitrogen, sulfur; or $NR^1$; R is COOH, $SO_3H$, $PO_3H_2$, or $P(O)(OH)R^4$. Further, in this general structure, each $R^1$, $R^2$, $R^3$ and $R^5$ is independently selected from a variety of substituent groups with most preferred $R^1$, $R^2$, $R^3$ and $R^5$ are $SR^6$, $R^8SR^6$, hydrogen, hydroxy and amino. At least one of $R^1$; $R^2$; $R^3$ or $R^5$ must be $SR^6$ or $R^8SR^6$. Most preferred $R^4$ is a $C_1$–$C_4$ alkyl and most preferred $R^5$ is hydrogen, halogen, amino or hydroxy. $R^6$ is most preferably H, $C(O)R^7$, $C(S)R^7$, $C(O)NR^7_2$, wherein $R^7$ is nil, hydrogen, or $C_1$–$C_8$ alkyl. Finally, in this general structure, when Q is S, N, $NR^1$, or O, the Q-containing chain is not attached to the heterocycle ring at the nitrogen atom of the heterocycle ring.

As stated above, it is essential that at least one of $R^1$, $R^2$, $R^3$ and $R^5$ is $SR^6$ or $R^8SR^6$; when any of $R^1$, $R^2$, $R^3$, or $R^5$ is $SR^6$ or $R^8SR^6$, the heterocyclic phosphonate is thio-substituted. Suitable thio-substituents in the compounds of the present invention are thiols, alkyl thiols, thioesters, alkyl thioesters, dithioesters, alkyl dithioesters, thiocarbamate, alkyl thiocarbamate, dithiocarbamate, alkyl dithiocarbamate, thiocarbonate, alkyl thiocarbonate, dithiocarbonate, and alkyl dithiocarbonates.

The present invention further relates to pharmaceutical compositions containing a safe and effective amount of a compound of the present invention, and pharmaceutically-acceptable excipients. Finally, the present invention relates to methods for treating or preventing pathological conditions characterized by abnormal calcium and phosphate metabolism in humans or other mammal. This method comprises administering to said human or other mammal in need of such treatment a safe and effective amount of a compound or composition of the present invention.

Definitions and Usage of Terms

The following is a list of definitions for terms used herein.

"Heteroatom" is a nitrogen, sulfur, or oxygen atom. Groups containing one or more heteroatoms may contain different heteroatoms.

"Alkyl" is an unsubstituted or substituted, straight-chain or branched, saturated or unsaturated hydrocarbon chain, said hydrocarbon chain may be saturated, having 1 to 8 carbon atoms, and preferably, unless otherwise stated, from 1 to 4 carbon atoms; said hydrocarbon chain may be unsaturated, having 2 to 8 carbon atoms, and preferably, unless otherwise stated, 2 to 4 carbon atoms. Accordingly, the term "alkyl", as used herein, encompasses alkenyl hydrocarbon unsaturated chains having at least one olefinic double bond and alkynyl hydrocarbon unsaturated chains having at least one triple bond. Preferred alkyl groups include, but are not limited to, methyl, ethyl, propyl, isopropyl, and butyl.

"Heteroalkyl" is an unsubstituted or substituted, saturated chain having from 3 to 8-members and comprising carbon atoms and one or two heteroatoms.

"Carbocyclic ring" or "Carbocycle" as used herein is an unsubstituted or substituted, saturated, unsaturated or aromatic, hydrocarbon ring, generally containing from 3 to 8 atoms, preferably from 5 to 7, atoms. Carbocyclic rings may be monocyclic, having from 3 to 8, preferably from 5 to 7, carbon atoms, or they may be polycyclic. Polycyclic carbocycles consisting of two rings generally have from 6 to 16, preferably from 10 to 12, atoms. Polycyclic carbocycles consisting of three rings generally contain from 13 to 17, preferably from 14 to 15, atoms.

"Heterocyclic ring" or "heterocycle" as used herein is an unsubstituted or substituted, saturated, unsaturated or aromatic ring comprised of 3 to 8, preferably 5–7 carbon atoms, and one or more additional heteroatoms in the ring. The term "heterocyclic ring moieties" as used herein encompasses monocyclic or polycyclic ring systems, fused or unfused, uusaturated, saturated or unsubstituted. Monocyclic heterocyclic ring moieties generally contain from 3 to 8 atoms, preferably from 5 to 7, atoms. Polycyclic heterocyclic ring moieties consisting of two rings generally contain from 6 to 16, preferably from 10 to 12, atoms. Polycyclic heterocyclic ring moieties consisting of three rings generally contain from 13 to 17 atoms, preferably from 14 to 15, atoms. In addition, a polycyclic heterocyclic ring moiety may consist solely of heterocycles (one of which must contain a nitrogen atom), or of both heterocycles (one of which must contain a nitrogen atom) and carbocycles. Each heterocyclic ring moiety must have at least one nitrogen atom. Unless otherwise stated, any additional heteroatom in the heterocyclic ring moiety may be independently chosen from nitrogen, sulfur, and oxygen.

"Aryl" is an aromatic carbocyclic ring. Preferred aryl groups include, but are not limited to, phenyl, tolyl, xylyl, cumenyl, and naphthyl.

"Heteroaryl" is an aromatic heterocyclic ring. Preferred heteroaryl groups include, but are not limited to, thienyl, furyl, pyrrolyl, pyridinyl, pyrazinyl, oxazolyl, thiazolyl, quinolinyl, pyrimidinyl, and tetrazolyl.

"Alkoxy" is an oxygen atom having a hydrocarbon chain substituent, where the hydrocarbon chain is an alkyl or alkenyl (e.g., —O-alkyl or —O-alkenyl). Preferred alkoxy groups include, but are not limited to, methoxy, ethoxy, propoxy, and alkyloxy.

"Hydroxyalkyl" is a substituted hydrocarbon chain which has a hydroxy substituent (e.g., —OH), and may have other substituents. Preferred hydroxyalkyl groups include, but are not limited to, hydroxyethyl, hydroxypropyl, and hydroxyalkyl.

"Carboxyalkyl" is a substituted hydrocarbon chain which has a carboxy substituent (e.g. —COOH) and may have other substituents. Preferred carboxyalkyl groups include carboxymethyl, carboxyethyl, and their acids and esters.

"Aminoalkyl" is a hydrocarbon chain (e.g. alkyl) substituted with an amine moiety (e.g., alkyl-NH—) such as methyl amine.

"Alkylamino" is an amino moiety having one or two alkyl substituents (e.g., —N-alkyl), such as dimethylamine.

"Alkenylamino" is an amino moiety having one or two alkenyl substituents (e.g., —N-alkenyl).

"Alkynalamino" is an amino moiety having one or two alkynyl substituents (e.g., —N-alkynyl).

"Alkylimino" is an imino moiety having one or two alkyl substituents (e.g., —N-alkyl—).

"Arylalkyl" is an alkyl moiety substituted with an aryl group. Preferred arylalkyl groups include benzyl and phenylethyl.

"Arylamino" is an amine moiety substituted with an aryl group (e.g., —NH-aryl).

"Aryloxy" is an oxygen atom having an aryl substituent (e.g., —O-aryl).

"Acyl" or "carbonyl" is a carbon to oxygen double bond, (e.g., R—C(=O)—). Preferred alkylacyl groups include, but are not limited to, acetyl, propionyl, butanoyl and benzoyl.

"Acyloxy" is an oxygen atom having an acyl substituent (e.g., —O-acyl); for example, —O—C(=O)-alkyl.

"Acylamino" is an amino moiety having an acyl substituent (e.g., —N-acyl); for example, —NH—(C=O)-alkyl.

"Halo", "halogen", or "halide" is a chloro, bromo, fluoro, or iodo atom radical. Chloro, bromo, and fluoro are preferred halides.

Also, as referred to herein, a "lower" hydrocarbon moiety (e.g., "lower" alkyl) is a hydrocarbon chain comprised of from, unless otherwise stated, 1 to 6, preferably from 1 to 4, carbon atoms.

As used herein, the term "thio-substituent" is depicted by $SR^6$ or $R^8SR^6$, wherein $R^8$ is a $C_1$–$C_8$ alkyl. Particular thio-substituents include thiol (—SH, where $R^6$=H); thioesters

where $R^6$ is $COR^7$); thiocarbamates

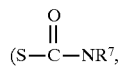

where $R^6$ is $CONR^7$); dithiocarbamates

where $R^6$ is $CSNR^7_2$); dithioesters

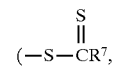

where $R^6$ is $CSR^7$); thiocarbonates

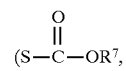

where $R^6$ is $C(O)OR^7$), and dithiocarbonates

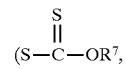

where $R^6$ is $C(S)OR^7$). $R^7$ as used herein is hydrogen or substituted or unsubstituted $C_1$–$C_8$ alkyl. It is to be understood that the $SR^6$ groups defined above can be preceded by an $R^8$ (i.e. a $C_1$–$C_8$ alkyl); this would yield alkyl thiols, alkyl thioesters, alkyl dithioesters, alkyl thiocarbamates, alkyl dithiocarbamates, alkyl thiocarbonates and alkyl dithiocarbonates.

The terms "bisphosphonate" or "bisphosphonic acid" as used herein relate to those phosphonate or phosphonic acids that have two phosphonate groups attached to the same carbon atom and are used interchangeably with the terms diphosphonate and diphosphonic acids. Using the structures described herein, in these compounds the moiety R is $PO_3H_2$.

A "pharmaceutically-acceptable" salt is a catonic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, hereby incorporated by reference herein. Preferred catonic salts include the alkali-metal salts (such as sodium and potassium), and alkaline earth metal salts (such as magnesium and calcium). Preferred anionic salts include the halide (such as chloride), acetates and phosphate salts.

A "biohydrolyzable ester" is an ester of thio-substituted phosphate compounds that does not interfere with the activity of the compounds, or that is readily metabolized by a human or other mammal to yield an active compound. Many such esters are known in the art, as described in World Patent Publication 87/05297, Johnston et al., published Sep. 11, 1987, and hereby incorporated by reference herein. Such esters include lower alkyl esters, lower acyloxyalkyl esters (such as acetoxymethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters).

As defined above and as used herein, substituent groups may themselves be substituted. Such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g. aminomethyl, etc.), cyano, halo, carboxy, alkoxyacetyl (e.g. carboethoxy, etc.), thio, thiol, aryl, cycloalkyl, heteroaryl, heterocycloalkyl (e.g., piperidinyl, morpholinyl, piperazinyl, pyrrolidinyl, etc.), imino, thioxo, hydroxyalkyl, aryloxy, arylalkyl, and combinations thereof.

DETAILED DESCRIPTION OF THE INVENTION

Thio-substituted, nitrogen-containing, heterocyclic phosphonate Compounds

The compounds of the present invention are thio-substituted heterocyclic phosphonic acids, and the pharmaceutically-acceptable salts and esters thereof, in which the phosphonic acid-containing carbon atom is linked to a carbon atom in a nitrogen-containing heterocyclic ring moiety, preferably a pyridine ring. The linkage from the phosphonic acid containing-carbon atom to the heterocyclic ring moiety may be direct through a covalent bond (preferably a single bond), or by a chain of length of from about 1 to about 10 atoms. If the linkage is via a linking chain, this chain may be all carbon atoms, a nitrogen atom or nitrogen-containing chain, an oxygen atom or oxygen-containing chain a sulfur atom or a sulfur-containing chain. The carbon and nitrogen atoms in the linking chains may, independently, be unsubstituted or substituted with one or more substituents selected from thio-substituents (including thiols, alkyl thiols, thioesters, alkyl thioesters, dithioesters, alkyl dithioesters, thiocarbamates, alkyl thiocarbamates, dithiocarbamates, alkyl dithiocarbamates, thiocarbonates, alkyl thiocarbonates, dithiocarbonates and alkyl dithiocarbonates), hydrogen, hydroxy, methyl, ethyl, or propyl. The carbon and nitrogen atoms in the chain may also be unsubstituted. Also preferred are chains one atom in length, i.e., —$CH_2$—, —NH—, and —O—.

For the compounds in which a nitrogen, sulfur or oxygen atom in the linking chain is bonded to the heterocycle ring moiety, this nitrogen, sulfur or oxygen atom is bonded to the ring at a carbon atom and not bonded directly to the ring's nitrogen atom. The present invention also includes those compounds in which a nitrogen atom in the linking chain is bonded to the heterocycle ring, when this nitrogen atom is bonded to a carbon atom bonded directly to a nitrogen atom in the heterocycle, then these compounds have an ylidene structure (as described more fully hereinafter). When Q is N, S, O, $NR^1$, and m=o, then Q is preferably bonded to the ring at a carbon atom. When Q is a covalent bond, then the linking chain may be bonded to either a carbon atom or a nitrogen atom in the ring.

The carbon atom which has the phosphonate group attached to it may be unsubstituted (i.e., a hydrogen atom), or substituted. The carbon atom may be substituted with two phosphonate groups (rendering a bisphosphonate compound); or with one phosphonate group and one phosphinate group (yielding a phosphonoalkylphosphinate compound); a phosphonate group and a sulfonate group (yielding a phosphonosulfonate compound); or a phosphonate group and a carboxylate group, (yielding a phosphonocarboxylate compound).

Furthermore, the carbon atoms in the heterocycle ring may be unsubstituted or substituted independently with one or more substituents. The nitrogen atom in the heterocycle ring may be unsubstituted or substituted.

It is essential that compounds of the present invention must have at least one thio-substituent, i.e. $SR^6$ or $R^8SR^6$ moieties. Accordingly, at least one of $R^1$, $R^2$, $R^3$, $R^3$, or $R^5$ must be $SR^6$ or $R^8SR^6$.

Thus, the thio-substituted, nitrogen-containing heterocyclic phosphonic acids of the present invention, and the pharmaceutically-acceptable salts and esters thereof, have the general structure:

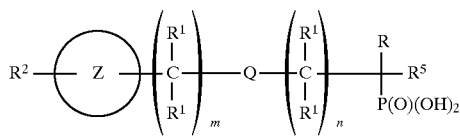

wherein m and n are integers 0 to 10 and m+n equals 0 to 10.

(a) Z is a monocyclic or polycyclic heterocyclic ring moiety containing one or more heteroatoms selected from O, S, or N, at least one of which is N;

(b) Q is covalent bond; O, S, N, or $NR^1$;

(c) R is COOH, $SO_3H$, $PO_3H_2$, or $P(O)(OH)R^4$; wherein $R^4$ is substituted or unsubstituted $C_1$–$C_8$ alkyl;

(d) each R1 is independently selected from —$SR^6$; —$R^8SR^6$; nil; hydrogen; unsubstituted or substituted $C_1$–$C_8$ alkyl; unsubstituted or substituted aryl; hydroxy; —$CO_2R^3$; —$O_2CR^3$; —$NR^3_2$; —$N(R^3)C(O)R^3$; —$OR^3$; —$C(O)N(R^3)_2$; substituted or unsubstituted benzyl; nitro; or combinations thereof;

(e) $R^2$ is one or more substituents on atoms in the Z moiety and is independently selected from —$SR^6$; —$R^8SR^6$; —$CO_2R^3$; —$O_2CR^3$; —$NR^3_2$; —$N(R)^3C(O)R^3$; $OR^3$; —$C(O)N(R^3)_2$; nil; hydrogen; unsubstituted or substituted $C_1$–$C_8$ alkyl; unsubstituted or substituted aryl; hydroxy; substituted or unsubstituted benzyl; nitro; or combinations thereof;

(f) each $R^3$ is independently selected from hydrogen; substituted or unsubstituted $C_1$–$C_8$ alkyl; or $R^8SR^6$;

(g) $R^5$ is selected from —$SR^6$; $R^8SR^6$; hydrogen; hydroxy; amino; halogen; unsubstituted or substituted $C_1$–$C_8$ alkyl; amino; halogen and (h) $R^6$ is independently selected from H; —$C(O)R^7$; —$C(S)R^7$; —$C(O)NR^7_2$; —$C(S)NR^7_2$; $C(O)(OR^7)$; or $C(S)(OR^7)$; wherein $R^7$ is hydrogen; or unsubstituted or substituted $C_1$–$C_8$ alkyl;

(i) $R^8$ is a substituted or unsubstituted $C_1$–$C_8$ alkyl; and at least one of $R^1$, $R^2$, $R^3$ or $R^5$ is $SR^6$ or $R^8SR^6$.

In this general structure, Z is a nitrogen-containing heterocyclic ring moiety. Said heterocyclic ring moiety may be a monocyclic ring system (i.e., one heterocyclic ring) or may be polycyclic ring system (i.e., one heterocyclic ring, and one or more heterocycle or carbocyclic rings). Each Z moiety must contain at least one nitrogen heteroatom and may contain one or more additional heteroatoms selected from oxygen, sulfur or nitrogen.

In these general structures, Q is a covalent bond, (preferably a single bond) or a moiety selected from oxygen, sulfur, nitrogen, or —$NR^1$—. Further, m and n and m+n are integers from about 0 to about 10, with m+n=0 or 1 being preferred; and m=0 and n=0 or 1 being more preferred for Q being oxygen, or —$NR^1$; and with m+n=0, 1, or 2 preferred for Q being a covalent bond.

The R moieties described herein may be COOH, $SO_3H$, $PO_3H_2$ or $P(O)(OH)R^4$, wherein $R^4$ is $C_1$–$C_8$ alkyl. When R is $PO_3H_2$, the thio-substituted phosphonate compound is a bisphosphonate; when R is $P(O)(OH)R^4$, the thio-substituted phosphonate compound is a phosphonoalkylphosphinate, when R is $SO_3H$, the thio-substituted phosphonate compound is a phosphonosulfonate; when R is COOH, the thio-substituted phosphonate compound is a phosphonocarboxylate.

As stated above, it is essential that at least one of $R^1$, $R^2$, $R^3$ or $R^5$ is $SR^6$ or $R^8SR^6$;, where any of $R^1$, $R^2$, $R^3$ and $R^5$ is $SR^6$ or $R^8SR^6$, the heterocyclic phosphonate is thio-substituted. Suitable thio-substituents for the compounds of the present invention include thiols, alkyl thiols, thioesters, alkyl thioesters, dithioesters, alkyl dithioesters, thiocarbamate, alkyl thiocarbamate, dithiocarbamate, alkyl dithiocarbamate, thiocarbonate, alkyl thiocarbonate, dithiocarbonate, and alkyl dithiocarbonate.

The $R^1$ moieties are substituents and are independently selected from thiol, alkyl thiol, thioesters, alkyl thioesters, dithioesters, alkyl dithioesters, thiocarbamate, alkyl thiocarbamate, dithiocarbamate, alkyl dithiocarbamate, thiocarbonates, alkyl thiocarbonates, dithiocarbonates, alkyl dithiocarbonates, hydrogen, halogen, $C_1$–$C_8$ alkyl, unsubstituted or substituted aryl, unsubstituted or substituted benzyl; hydroxy; —C(O)N($R^3$)$_2$; —O$R^3$; —CO$_2R^3$; —O$_2$C$R^3$; N$R^3_2$; —N($R^3$)C(O)$R^3$; nitro; and combinations thereof; wherein $R^3$ is independently selected from $R^8SR^6$, hydrogen, or substituted or unsubstituted $C_1$–$C_8$ alkyl, preferably thio-substituted alkyls. When Q is a covalent bond and any $R^1$ is nil, an adjacent $R^1$ must be nil; this indicates an unsaturated chain when Q is N$R^1$, $R^1$ may be nil to indicated a carbon to nitrogen double bond.

However, when n=0 and Q is oxygen, sulfur, or nitrogen, then $R^5$ is selected from hydrogen; alkyl having from about 1 to about 8 carbon atoms; $R^8SR^6$, the pharmaceutically-acceptable salts and esters thereof; and combinations thereof.

Preferred $R^1$ is selected from thio-substituents, hydrogen, chloro, methyl, ethyl, hydroxy, unsubstituted amino, (N-methyl)amino, (N, N-dimethyl)amino, —CO$_2$H and the pharmaceutically-acceptable salts thereof, —CO$_2$CH$_3$ and —CONH$_2$. More preferred $R^1$ is selected from thiol, (or thio-containing substituents), hydrogen, methyl, chloro, amino, and hydroxy. Most preferred $R^1$ is thiol, hydrogen, hydroxy, or amino. In addition, as stated hereinabove, it is essential that the compounds of the present invention, at least one of $R^1$, $R^2$, $R^3$ and $R^5$ be a thio-containing substituent, i.e. $SR^6$ or $R^8SR^6$.

The heterocyclic ring moiety in the compounds of the present invention may be unsubstituted or substituted on the atoms of the ring independently with one or more substituents ($R^2$). The $R^2$ groups may be on the same carbon atom, or on different atoms of the heterocycle ring moiety.

Thus, the $R^2$ groups are substituents, on one or more atoms of the heterocycle, and are independently selected from nil; $SR^6$; $R^8SR^6$; hydrogen; halogen; $C_1$–$C_8$ alkyl; unsubstituted or substituted aryl; unsubstituted or substituted benzyl; —C(O)N($R^3$)$_2$; —O$R^3$; —CO$_2R^3$; —O$_2$C$R^3$; —N$R^3_2$; —N($R^3$)C(O)$R^3$; nitro, and combinations thereof, wherein $R^3$ is independently selected from hydrogen, or unsubstituted or substituted $C_1$–$C_8$ alkyl, preferably thio-substituted alkyl.

Preferred $R^2$ substituents are independently selected from thio-substituents; ($SR^6$, $R^8SR^6$), hydrogen, methyl, ethyl, hydroxy unsubstituted amino, (N-methyl)amino, (N,N-dimethyl)amino, chloro, methoxy, ethoxy, nitro, —CO$_2$H and the pharmaceutically-acceptable salts thereof, —CO$_2$CH$_3$, CONH$_2$, and combinations thereof. More preferred $R^2$ substituents are independently selected from thio-containing substituents; hydrogen, methyl, amino, chloro, methoxy, hydroxy and combinations thereof. Most preferred $R^2$ substituents are independently selected from thio-containing substituents; hydrogen and methyl. In addition, as stated hereinabove, it is essential that in the compounds of the present invention, at least one of $R^1$, $R^2$, $R^3$ and $R^5$ be a thio-containing substituent, i.e. $SR^6$ or $R^8SR^6$.

$R^5$ in the general structure hereinabove denotes hydrogen, halogen, hydroxy, amino, thio-substituents, i.e. $SR^6$ or $R^8SR^6$, unsubstituted or substituted $C_1$–$C_8$ alkyl. Preferred $R^5$ is hydroxy, amino, hydrogen, halogen, thio; most preferred $R^5$ is hydroxy, amino, and hydrogen.

$R^6$ denotes a substituent on the sulfur-containing substituent, —$SR^6$. $R^6$ is hydrogen; —C(O)$R^7$; —C(S)$R^7$; —C(O)N$R^7_2$; —C(S)N$R^7_2$; —C(O)O$R^7$, —C(S)O$R^7$, wherein $R^7$ is nil, hydrogen, or unsubstituted or substituted $C_1$–$C_8$ alkyl. Preferred $R^6$ is H, C(O)$R^7$, C(O)N$R^7$; most preferred $R^6$ is hydrogen. Preferred $R^7$ is hydrogen or $C_1$–$C_8$ alkyl.

The Z moiety of the present invention is a nitrogen-containing heterocyclic ring moiety. Said heterocyclic ring moiety has one or more heteroatoms selected from O, S, or N, at least one of which is nitrogen. The Z moiety may be a monocyclic heterocyclic ring moiety having from 3 to 8 atoms or may be a polycyclic heterocyclic ring moiety having 6 to 17 atoms. Said polycyclic ring moiety may contain two or more heterocycles, or one heterocycle and one more more carbocyclic rings; however, at least one ring in the heterocyclic ring moiety must have at least one nitrogen atom; accordingly there must be at least one nitrogen-containing heterocycle in the heterocyclic ring moiety.

Preferred monocyclic Z moieties are pyrimidine, pyrazine, piperidine, and pyridine.

Preferred polycyclic Z moieties are quinolines, pyrrolopyridines, quinoxalines and imidazo(N) pyridines.

Furthermore in the hereinbefore general structures, when m=0 and Q is oxygen, or nitrogen, then the bonding of the Q moiety to the heterocycle ring is preferably limited as follows. The Q moiety is bonded to the heterocycle ring at a carbon atom not bonded directly to a nitrogen atom in the heterocycle-ring (e.g., the 3, 4, or 5 positions of a piperidine ring when counting the nitrogen atom as the 1 position of the ring), except that when Q is nitrogen, then Q may also be bonded to the heterocycle ring by an ylidene structure. A compound of the present invention having an ylidene structure comprises a N=C—N chemical bonding as part of the heterocycle ring.

The preferred thio-substituted, pyridine-containing bis-phosphonic acid compounds of the present invention may have the following general structures:

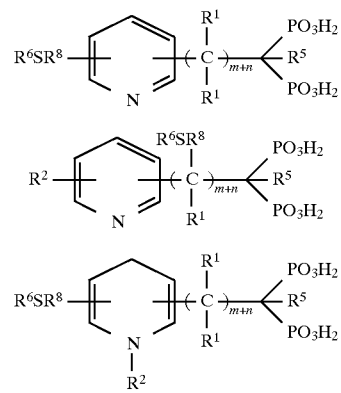

Also preferred are thio-substituted, pyridine-containing bisphosphonates wherein the linking chain has a heteroatom, i.e. Q=S, O, N, or N$R^1$.

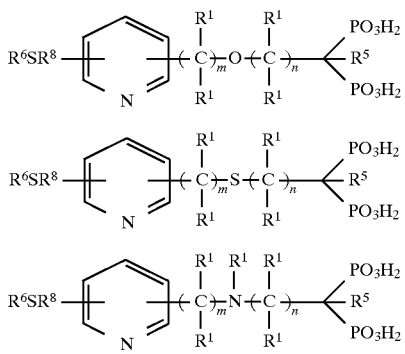

In addition, the thio-substituted piperidine bisphosphonic acids, and the pharmaceutically-acceptable salts and esters thereof, of the present invention may alternatively have the following general structures:

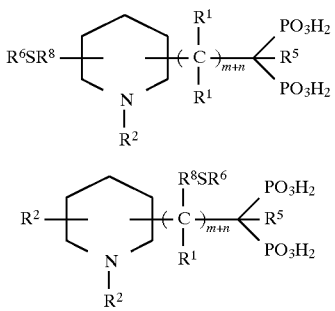

Other thio-substituted bisphosphonic acid compounds include those compounds wherein the Z moiety is a polycyclic heterocyclic ring moiety consisting of two rings.

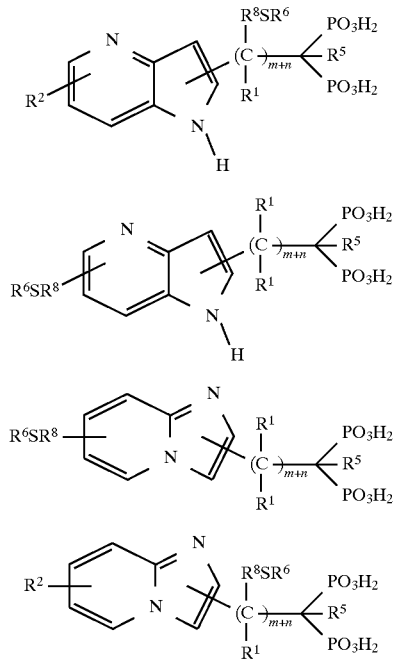

Other preferred thio-containing heterocycle substituted bisphosphonic acids, are those compounds where the Z moiety is a pyrimidine. These compounds, and the pharmaceutically acceptable salts and esters thereof, have the general structures:

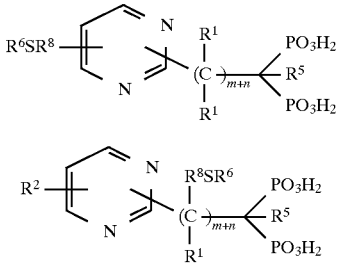

Other suitable thio-substituted heterocyclic bisphosphonic acids include those compounds wherein Z is a seven-membered nitrogen-containing heterocycle, having the following general structure:

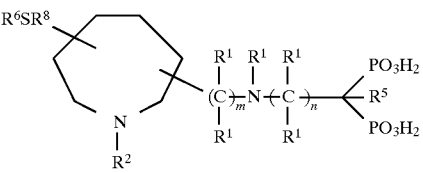

Thio-substituted heterocyclic bisphosphonic acids wherein the Z moiety is a five-membered heterocycle are also preferred and may have the following general structure:

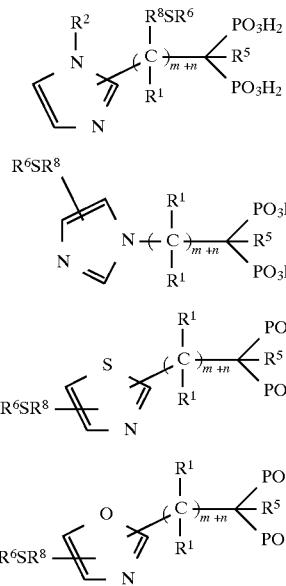

wherein $R^2$ is selected from hydrogen or methyl, with preferred $R^2$ being hydrogen; and $R^3$ and $R^4$ are substituents independently selected from the group consisting of hydrogen, methyl, amino, chloro, methoxy, hydroxy, and combinations thereof, with most preferred $R^3$ and $R^4$ being hydrogen or methyl.

Specific examples of compounds of the present invention include:
[(5[mercaptomethyl]-2-piperidinyl)methylene]bis[phosphonic acid; [(5-mercaptomethyl-3-piperidinyl)methylene]bis[phosphonic acid; [(5-mercapto-2-piperidinyl]methylene)bis[phosphonic acid; [(5-[4-mercaptobutyl]-2-piperidinyl)methylene]bis[phosphonic acid; [(5-mercapto-3-piperidinyl]methylene)bis[phosphonic acid; [(5-[5-mercaptopentyl]-3-piperidinyl)methylene]bis[phosphonic acid; [(5-[2-mercaptoethyl]-4-piperidinyl)methylene]bis[phosphonic acid; [5-mercapto-4-piperidinyl)methylene]bis[phosphonic acid; [2-(5-mercapto-2-piperidinyl)ethylidene]bis[phosphonic acid]; [2-(5-[3-mercaptopropyl]-2-piperidinyl)ethylidene]bis[phosphonic acid]; [2-(5-mercapto-3-piperidinyl)ethylidene]bis[phosphonic acid]; [2-(5-mercapto-4-piperidinyl)ethylidene]bis[phosphonic acid]; [2-(5-[4-mercaptobutyl]-2-piperidinyl)ethylidene]bis[phosponic acid]; [2-(5-mercaptomethyl-3-piperidinyl)ethylidene]bis[phosphonic acid]; [(2-[5-mercapto-2-piperidinyl]-1-hydroxy)ethylidene]bis[phosphonic acid]; [(2-[5-(3-mercaptopropyl)-2-piperidinyl]-1-hydroxy)ethylidene]bis[phosphonic acid] [(2-[5-mercapto-3-piperidinyl]-1-hydroxy)ethylidene]bis[phosphonic acid]; [(2-[5-(2-mercaptoethyl)-3-piperidinyl]-1-hydroxy)ethylidene]-bis[phosphonic acid]; [(2-[5-mercapto-4-piperidinyl]-1-hydroxy)ethylidene]bis[phosphonic acid]; [(2-[5-mercaptomethyl-4-piperidinyl]-1-hydroxy)ethylidene]bis[phosphonic acid]; [(2-[5-mercaptomethyl-3-methyl-2-piperidinyl]-1-hydroxy)-ethylidene]bis[phosphonic acid]; [(2-[5-mercapto-3-methyl-2-piperidinyl]-1-hydroxy)-ethylidene]bis[phosphonic acid]; [(2-[3-mercaptomethyl-5-methyl-2-piperidinyl]-1-hydroxy)-ethylidene]bis[phosphonic acid]; [2-(5-mercaptomethyl-3-methyl-2-piperidinyl)-ethylidene]bis[phosphonic acid]; [2-(3-mercaptomethyl-5-methyl-2-piperidinyl)-ethylidene]bis[phosphonic acid]; [3-[5-(mercaptomethyl)-2-piperidinyl]propylidene]bis[phosphonic acid]; [3-[5-(mercaptomethyl)-3-piperidinyl]propylidene]bis[phosphonic acid]; [3-[5-(mercaptomethyl)-4-piperidinyl]propylidene]bis[phosphonic acid]; [3-[5-(mercaptomethyl)-2-piperidinyl]-1-hydroxypropylidene]bis[phosphonic acid]; [3-[5-mercapto-3-piperidinyl]-1-hydroxypropylidene]-bis[phosphonic acid]; [3-[5-(4-mercaptobutyl)-4-piperidinyl]-1-hydroxypropylidene]-bis[phosphonic acid]; [2-(3-mercaptomethyl-5-methyl-2-pyridinyl)ethylidene]-bis[phosphonic acid]; [2-(5-[3-mercaptopropyl]-2-methyl-2-piperidinyl)ethylidene]bis[phosphonic acid]; [(2-[5-(2-mercaptopropyl)-2-piperidinyl]-1-amino)ethylidene]bis[phosphonic acid]; [(2-[5-(3-mercaptopropyl)-3-piperidinyl]-1-amino)ethylidene]bis[phosphonic acid]; [2-(5-[3-mercaptopropyl]-4-piperidinyl)-1-aminoethylidene]bis[phosphonic acid]; [(2-[3-methyl-5-(3-mercaptopropyl)-2-piperidinyl]-1-hydroxy)-ethylidene]bis[phosphonic acid]; [(2-[3-amino-5-(3-mercaptopropyl)-2-piperidinyl]-1-hydroxy)ethylidene]bis[phosphonic acid]; [2-[5-mercapto-2-(1,4-diazinyl)]ethylidene]bis[phosphonic acid]; [2-[5-(3-mercaptopropyl)-2-(1,4-diazinyl)]ethylidene]bis[phosphonic acid]; [2-[5-(3-mercaptopropyl)-2-(1,4-diazinyl)]-1-hydroxyethylidene]bis[phosphonic acid]; [2-[5-mercapto-2-(1,4-diazinyl)]-1-hydroxyethylidene]bis[phosphonlc acid]; [2-[5-mercapto-2-(1,3-diazinyl)]ethylidene]bis[phosphonic acid] [2-[5-(3-mercaptopropyl)-2-(1,3-diazinyl)]ethylidene]bis[phosphonic acid]; [2-[5-(3-mercaptopropyl)-2-(1,3-diazinyl)]-1-hydroxyethylidene]bis[phosphonic acid]; [2-[5-mercapto-2-(1,3-diazinyl)]-1-hydroxyethylidene]bis[phosphonic acid]; [(5-[3-mercaptopropyl]-2-piperidinyl)aminomethylene]bis[phosphonic acid]; [(5-mercapto-2-piperidinyl)aminomethylene]bis[phosphonic acid]; [(5-[3-mercaptopropyl]-3-piperidinyl)aminomethylene]bis[phosphonic acid]; [(5-mercapto-3-piperidinyl)aminomethylene]bis[phosphonic acid]; [(5-mercapto-4-piperidinyl)aminomethylene]bis[phosphonic acid]; [(5-[3-mercaptopropyl]-4-piperidinyl)aminomethylene]bis[phosphonic acid]; [(5-mercapto-3-methyl-2-piperidinylidene)aminomethylene]bis[phosphonic acid]; [(5-[3-mercaptopropyl]-3-methyl-2-piperidinylidene)aminomethylene]bis[phosphonic acid]; [2-(5-mercapto-3-methyl-2-piperidinylidene)aminoethylene]bis[phosphonic acid]; [2-(5-[3-mercaptopropyl]-3-methyl-2-piperidinylidene)aminomethylene]bis[phosphonic acid]; [(5-mercapto-2-piperidinylidene)aminomethylene]bis[phosphonic acid]; [(5-[3-mercaptopropyl]-2-piperidinylidene)aminomethylene]bis[phosphonic acid]; [2-(5-mercapto-2-piperidinylidene)aminoethylene]bis[phosphonic acid] [(5-[3-mercaptopropyl]-2-piperidinylidene)aminomethylene]bis[phosphonic acid]; [(5-[3-mercaptopropyl]-2-[1,4-diazinylidene])aminomethylene]bis[phosphonic acid]; [(5-[3-mercaptopropyl]-2-[1,3-diazinylidene])aminomethylene]bis[phosphonic acid]; [(4-[3-mercaptopropyl]-2-[1,3,5-triazinylidene])aminomethylene]bis[phosphonic acid]; N-(2'-(1', 3'-diazinylidene))-aminomethane diphosphonic acid; and the pharmaceutically-acceptable salts and esters thereof.

In order to determine and assess pharmacological activity, testing of the diphosphonate compounds in animals is carried out using various assays known to those skilled in the art. Thus, the In vivo bone antiresorptive activity may be conveniently demonstrated using an assay designed to test the ability of these compounds to inhibit the resorption of bone, which bone resorption is characteristic of abnormal calcium and phosphate metabolism. Examples of such known tests include the Schenk model rat model and the adjuvant arthritis test. Also useful is the in vitro hydroxyapatite crystal growth inhibition test. These and other appropriate tests for pharmacological activity are disclosed and/or referred to in Shinoda et al., *Calcified Tissue International*, 35, pp 87–99 (1983); Schenk et al. *Calcified Tissue Research*, 11, pp 196–214 (1973); Russell et al., *Calcified Tissue Research*, 6, pp 183–196 (1970); Muhlbauer and Fleisch, *Mineral Electrolyte Metab.*, 5, pp 296–303 (1981); Nancollas et al., Oral Biol., 15, 731 (1970); U.S. Pat. No. 3,683,080, to Francis, issued Aug. 8, 1972; U.S. Pat. No. 4,134,969, to Schmidt-Dunker, Issued Jan. 16, 1979; and EPO Patent Application Publication No. 189,662, published August 6, 1986; the disclosures of all these articles and patent specifications being incorporated herein by reference in their entirety. Certain of these tests for pharmacological activity are also described in more detail in the Examples provided hereinafter.

In addition to being useful for treating or preventing pathological conditions characterized by abnormal calcium or phosphate metabolism, the compounds of the present invention may have other uses. For example, the compounds of the present invention are believed to be useful as bone scanning agents after labeling with 99m-technetium. In addition, the compounds of the present invention are useful as sequestering agents for polyvalent metal ions, particularly di (e.g. calcium and magnesium).—and trivalent metal ions (e.g. indium). Thus, the compounds of the present invention are useful as builders in detergents and cleansers, or for treating water. They are also useful as stabilizers for compounds. In addition, they may be useful in preventing the formation of tartar (i.e., calculus) and/or plaque on teeth. Finally, the compounds of the present invention may be useful as herbicides which are non-toxic to animals.

The thio-substituted, nitrogen-containing heterocyclic phosphonate compounds of the present invention can be made utilizing the methods set forth in Examples A–H herein.

Compositions Containing Novel Thio-Substituted, Nitrogen-Containing Heterocyclic Phosphonate Compounds The novel thio-substituted phosphonate compounds of the present invention may be administered to humans or other mammals by a variety of routes, including, but not limited to, oral dosage forms and injections (intravenous, intramuscular, intraperitoneal and subcutaneous). Numerous other dosage forms containing the novel thio-substituted phosphonate compounds of the present invention can be readily formulated by one skilled in the art, utilizing the suitable pharmaceutical excipients as defined below. For considerations of patient compliance, oral dosage forms are generally most preferred.

The term "pharmaceutical composition" as used herein means a combination comprised of a safe and effective amount of the thio-substituted phosphonate compound active ingredient, or mixtures thereof, and pharmaceutically-acceptable excipients.

The phrase "safe and effective amount", as used herein, means an amount of a compound or composition large enough to significantly positively modify the symptoms and/or condition to be treated, but small enough to avoid serious side effects (at a reasonable benefit/risk ratio), within the scope of sound medical judgment. The safe and effective amount of active ingredient for use in the pharmaceutical compositions to be used in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular phosphonate compound active ingredient selected for use. Pharmaceutically-acceptable excipients include, but are not limited to, polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

The term "oral dosage form" as used herein means any pharmaceutical composition intended to be systemically administered to an individual by delivering said composition to the gastrointestinal tract of an individual, via the mouth of said individual. For purposes of the present invention, the delivered form can be in the form of a tablet, coated or non-coated; solution; suspension; or a capsule, coated or non-coated.

The term "injection" as used herein means any pharmaceutical composition intended to be systemically administered to a human or other mammal, via delivery of a solution or emulsion containing the active ingredient, by puncturing the skin of said individual, in order to deliver said solution or emulsion to the circulatory system of the individual either by intravenous, intramuscular, intraperitoneal or subcutaneous injection.

The rate of systemic delivery can be satisfactorily controlled by one skilled in the art, by manipulating any one or more of the following:

(a) the active ingredient proper;
(b) the pharmaceutically-acceptable excipients; so long as the variants do not interfere in the activity of the particular active ingredient selected;
(c) the type of the excipient, and the concomitant desirable thickness and permeability (swelling properties) of said excipients;
(d) the time-dependent conditions of the excipient itself and/or within the excipients;
(e) the particle size of the granulated active ingredient; and
(f) the pH-dependent conditions of the excipients.

In particular, the solubility, acidity, and susceptibility to hydrolysis of the different thio-substituted phosphonate active ingredients, such as acid addition salts, salts formed with the carboxylic group, e.g., alkali metal salts, alkaline earth metal salts, etc., and esters, e.g., alkyl, alkenyl, aryl, aralkyl, may be used as guidelines for the proper choice. In addition, suitable pH-conditions might be established within the oral dosage forms by adding a suitable buffer to the active ingredient in accordance with the desired release pattern.

As stated hereinabove, pharmaceutically-acceptable excipients include, but are not limited to, resins, fillers, binders, lubricants, solvents, glidants, disintegrants cosolvents, surfactants, preservatives, sweetener agents, flavoring agents, buffer systems, pharmaceutical-grade dyes or pigments, and viscosity agents.

The preferred solvent is water.

Flavoring agents among those useful herein include those described in *Remington's Pharmaceutical Sciences*, 18th Edition, Mack Publishing Company, 1990, pp. 1288–1300, incorporated by reference herein. The pharmaceutical compositions suitable for use herein generally contain from 0–2% flavoring agents.

Dyes or pigments among those useful herein include those described in *Handbook of Pharmaceutical Excipients*, pp. 81–90, 1986 by the American Pharmaceutical Association & the Pharmaceutical Society of Great Britain, incorporated by reference herein. The pharmaceutical compositions herein generally contain from 0–2% dyes or pigments.

Preferred co-solvents include, but are not limited to, ethanol, glycerin, propylene glycol, polyethylene glycols. The pharmaceutical compositions of the present invention include from 0–50% co-solvents.

Preferred buffer systems include, but are not limited to, acetic, boric, carbonic, phosphoric, succinic, malaic, tartaric, citric, acetic, benzoic, lactic, glyceric, gluconic, glutaric and glutamic acids and their sodium, potassium and ammonium salts. Particularly preferred are phosphoric, tartaric, citric, and acetic acids and salts. The pharmaceutical composition of the present invention generally contain from 0–5% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids. The pharmaceutical compositions of the present invention include 0–2% surfactants.

Preferred preservatives include, but are not limited to, phenol, alkyl esters of parahydroxybenzoic acid, o-phenylphenol benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben. The compositions of the present invention generally include from 0–2% preservatives.

Preferred sweeteners include, but are not limited to, sucrose, glucose, saccharin, sorbitol, mannitol, and aspartame. Particularly preferred are sucrose and saccharin. Pharmaceutical compositions of the present invention include 0–5% sweeteners.

Preferred viscosity agents include, but are not limited to, methylcellulose, sodium carboxymethylcellulose, hydroxypropylmethylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0–5% viscosity agents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0–75% fillers.

Preferred lubricants include, but are not limited to, magnesium stearate, stearic acid, and talc. The pharmaceutical compositions of the present invention include 0.5–2% lubricants.

Preferred glidants include, but are not limited to, talc and colloidal silicon dioxide. The compositions of the present invention include from 1–5% glidants.

Preferred disintegrants include, but are not limited to, starch, sodium starch glycolate, crospovidone, croscarmelose sodium, and microcrystalline cellulose. The pharmaceutical compositions of the present invention include from 4–15% disintegrants.

Preferred binders include, but are not limited to, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. The compositions of the present invention include 1–10% binders.

Compounds of the present invention may comprise from about 0.1% to about 99.9% by weight of the pharmaceutical compositions of the present invention. Preferably, the compounds of the present invention comprise from about 15% to about 95% by weight of the pharmaceutical compositions of the present invention.

Accordingly, the pharmaceutical compositions of the present invention include from 15–95% of a thio-substituted phosphonate compound active ingredient, or mixture, thereof; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

The choice of a pharmaceutical excipient to be used in conjunction with the thio-substituted phosphonates of the present compositions is basically determined by the way the phosphonate compound is to be administered. If the compound is to be injected, the preferred pharmaceutical carrier is sterile, physiological saline, the pH of which has been adjusted to about 7.4. However, the preferred mode of administering the phosphonates of the present invention is orally, and the preferred unit dosage form is therefore tablets, capsules and the like, comprising from about 0.1 mg P to about 600 mg P of the diphosphonic acid compounds described herein. Pharmaceutical carriers suitable for the preparation of unit dosage forms for oral administration are well known in the art. Their selection will depend on secondary considerations like taste, cost, and shelf stability, which are not critical for the purposes of the present invention, and can be made without difficulty by a person skilled in the art.

The term "mg P", as used herein, means the weight of the phosphorus atoms present in an amount of a diphosphonic acid compound of the present invention. This unit is used to standardize the amount of the diphosphonic acid compounds of the present invention to be used in the pharmaceutical compositions and methods of the present inventions. For example, [[5-[(2-Mercapto-1-oxopropylamino-2-pyridinyl] aminomethylene]bis[phosphonic acid] has a molecular weight of 371 g/mole, of which 16.7% (62 g/mole) is due to the two phosphorus atoms present in this molecule. One milligram of this compound is therefore calculated to have 0.17 mg P (1 mg×16.7%). Thus, to prepare a pharmaceutical composition containing 1 mg P of this compound, the composition should contain 6 mg of the compound; and to dose 1 mg P/kg of this compound to a 50 kg patient, the patient would be dosed with 300 mg of this compound.

The pharmaceutically-acceptable carrier employed in conjunction with the phosphonates of the present invention is used at a concentration sufficient to provide a practical size to dosage relationship. Preferably, the pharmaceutically-acceptable carriers, in total, may comprise from about 0.1% to about 99.9% by weight of the total composition and more preferably from about 20% to about 80%.

Suitable pharmaceutical compositions are described herein in Examples J–L. It is well within the capabilities of one skilled in the art to vary the non-limiting examples described herein to achieve a broad range of pharmaceutical compositions.

Method for Treating or Preventing Diseases Characterized by Abnormal Calcium and Phosphate Metabolism Another aspect of the present invention is methods for treating or preventing diseases characterized by abnormal calcium and phosphate metabolism. Such methods comprise administering to a human or lower animal in need of such treatment a safe and effective amount of diphosphonate compound of the present invention.

The preferred mode of administration is oral, but other known methods of administration are contemplated as well, e.g., dermatomucosally (for example, dermally, rectally and the like) and parenterally (for example, by subcutaneous injection, intramuscular injection, intra-articular injection, intravenous injection and the like). Inhalation is also included. Thus, specific modes of administration include, without limitation, oral, transdermal, mucosal, sublingual, intramuscular, intravenous, intraperitoneal, and subcutaneous administration, as well as topical application.

The term "abnormal calcium and phosphate metabolism", as used herein, means (1) conditions which are characterized by anomalous mobilization of calcium and phosphate leading to general or specific bone loss, or excessively high calcium and phosphate levels in the fluids of the body; and (2) conditions which cause or result from deposition of calcium and phosphate anomalously in the body. The first category includes, but is not limited to, osteoporosis, Paget's disease, hyperparathyroidism, hypercalcemia of malignancy, heterotopic ossification, and osteolytic bone metastases. The second category includes, but is not limited to, myositis ossificans progressiva, calcinosis universalis, and such afflictions as arthritis, rheumatoid arthritis, osteoarthritis, neuritis, bursitis, tendonitis and other which predispose involved tissue to deposition of calcium and phosphate.

The term "rheumatoid arthritis" as used herein, means a chronic systemic and articular inflammatory disorder of unknown etiology. It is characterized by destruction of articular cartilage, ligaments, tendons, and bone.

The term "osteoarthritis" as used herein, means a non-inflammatory disorder of the movable joints. It is characterized by deterioration and abrasion of the articular cartilage; and new bone formation at the joint surface.

The terms "person at risk" and "person in need of such treatment", as used herein, mean any human or other mammal which suffers a significant risk of abnormal calcium and phosphate metabolism if left untreated, and any human or other mammal diagnosed as being afflicted with abnormal calcium and phosphate metabolism. For example, post-menopausal women; persons undergoing certain steroid therapy; persons on certain anti-convulsant drugs; persons diagnosed as having Paget's disease, hyperparathyroidism, hypercalcemia of malignancy, or osteolytic bone metastases; persons diagnosed as suffering from one or more of the various forms of osteoporosis; persons belonging to a population group known to have a significantly higher than average chance of developing osteoporosis, e.g., postmenopausal women, men over age 65, and persons being treated with drugs known to cause osteoporosis as a side effect; persons diagnosed as suffering from myositis ossificans progressiva or calcinosis universalis; and persons afflicted with arthritis, osteoarthritis, neuritis, bursitis, tendonitis and other inflammatory conditions which predispose involved tissue to deposition of calcium and phosphate.

The phrase "safe and effective amount", as used herein, means an amount of a compound or composition of the present invention high enough to significantly positively modify the condition to be treated, but low enough to avoid serious side effects (at a reasonable benefit/risk ratio), within the scope of sound medical judgment. The safe and effective amount of diphosphonate compounds of the present invention will vary with the particular condition being treated, the age and physical condition of the patient being treated, the severity of the condition, the duration of the treatment, the nature of concurrent therapy, the specific phosphonate employed, the particular pharmaceutically-acceptable excipients utilized, and like factors within the knowledge and expertise of the attending physician. However, single dosages can range from about 0.01 mg P to about 3500 mg P, or from about 0.0002 to about 70 mg P/kg of body weight (based on a body weight of 50 kg). Preferred single dosages are from about 1 mg P to about 600 mg P, or from about 0.02 to about 12 g P/kg of body weight (based on a body weight of 50 kg). Up to about four single dosages per day may be administered. Daily dosages greater than about 500 mg P/kg are not required to produce the desired effect and may produce undesirable side effects. The higher dosages within this range are, of course, required in the case of oral administration because of limited absorption.

The following Examples further describe and demonstrate the preferred embodiments within the scope of the present invention. The Examples are given solely for the purpose of illustration, and are not to be construed as limitations of the present invention since many variations thereof are possible without departing from its spirit and scope.

EXAMPLE A

Synthesis of [(5-(3-Mercaptopropyl)-2-pyridinyl) aminomethylene]bis[phosphonic acid]

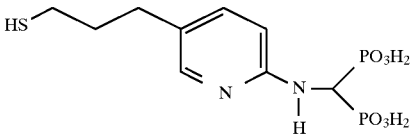

The compound above is prepared and synthesized as described hereinbelow.

I. Synthesis of [(5-Bromo-2-pyridinyl)aminomethylene]bis[phosphonic acid] tetraethyl ester 2-Amino-5-bromopyridine (12.5 g, 72 mmol), triethylorthoformate (79.2 mmol) and diethylphosphite (158.4 mmol) are heated at 140° C. in a round bottom flask fitted with a distillation head to collect ethanol throughout the course of the reaction. After heating 8 hours, the reaction mixture is cooled and then concentrated under reduced pressure. The desired product is obtained by flash chromatography with 5% isopropanol in methylene chloride on silica gel.

II. Synthesis of [(5-(3-Hydroxypropyl-2-pyridinyl) aminomethylene]bis[phosphonic acid] tetraethyl ester To a solution of [(5-bromo-2-pyridinyl)aminomethylene]bis[phosphonic acid] tetraethyl ester(10 mmol) in THF (10 ml) cooled to −78° C. is added a solution of n-butyllithium (2.1 equivalent) in hexane over 30 minutes. The reaction is kept at −78° C. for an additional 30 minutes. To this solution is added 3-iodopropanol trimethylsilyl (TMS) ether (2.5 equivalent) and the reaction is allowed to warm to room temperature over 30 minutes. After standard aqueous workup, [(5-(3-hydroxypropyl, TMS ether)-2-pyridinyl) aminomethylene]bis[phosphonic acid] tetraethyl ester is isolated and used in the next reaction without purification.

Cleavage of the TMS ether from the product is accomplished by stirring it in THF and adding a solution of tetrabutylammonuim fluoride (1M in THF) dropwise over 30 minutes. After a standard aqueous workup the resulting primary alcohol is isolated as an oil and used directly in the next reaction.

III. Synthesis of [(5-(3-Bromopropyl)-2-pyridinyl)aminomethylene]bis[phosphonic acid] tetraethyl ester A mixture of [(5-(3-hydroxypropyl)-2-pyridinyl) aminomethylene]-bis(phosphonic acid) tetraethyl ester (10 mmol), carbon tetrabromide (11 mmol) and triphenyl phosphine (11 mmol) in dichloromethane (100 ml) is stirred at room temperature for 5 h. Water is added and the product is extracted with dichloromethane. The combined organic extracts are dried and concentrated. The residue is purified by flash column chromatography to give [(5-(3-bromopropyl)-2-pyridinyl)aminomethylene]bis[phosphonic acid] tetraethyl ester.

IV. Synthesis of [(5-(3-Acetylthiopropyl)-2-pyridinyl) aminomethylene]bis[phosphonic acid] tetraethyl ester A solution of [(5-(3-bromopropyl)-2-pyridinyl) aminomethylene]bis[phosphonic acid] tetraethyl ester (5.0 mmol) is stirred in dry acetone (35 ml) and sodium thioacetate (5.2 mmol) is added. The mixture is stirred at 50° C. for 12 hours. After cooling to room temperature the solvent is removed under reduced pressure. The crude residue is dissolved in methylene chloride and washed with water. The organic layer is then dried and concentrated under reduced pressure. The desired product is purified by flash chromatography using a 5–10% isopropanol in methylene chloride gradient on silica gel.

V. Synthesis of [(5-(3-Mercaptopropyl)-2-pyridinyl) aminomethylene]bis[phosphonic acid]

The thioacetate (4.2 mmol) is heated at reflux in 1N HCl (15 ml) for 5 hours. The reaction mixture is cooled, treated with charcoal, filtered and concentrated under reduced pressure. The desired product is obtained in suitable purity following trituration with acetone and further drying under vacuum overnight.

EXAMPLE B
Synthesis of [(5-(3-Acetylthiopropyl)-2-pyridinyl) aminomethylene]bis[phosphonic acid]

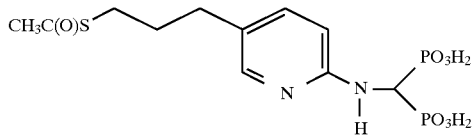

[(5-(3-Acetylthiopropyl)-2-pyridinyl)aminomethylene]-bis[phosphonic acid] is prepared by heating [(5-(3-acetylthiopropyl)-2-pyridinyl)aminomethylene]bis [phosphonic acid] tetraethyl ester [prepared as described in Example A (part III) hereinbefore] at reflux in distilled water for 18 hours under an atmosphere of argon. The reaction mixture is concentrated under reduced pressure and the product is obtained by recrystallization from water and isopropanol.

EXAMPLE C
Synthesis of [(5-Mercapto-2-pyridinyl) aminomethylene]bis [phosphonic acid]

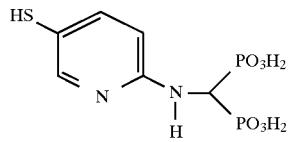

The compound above is prepared and synthesized as described hereinbelow.

I. Synthesis of [(5-Nitro-2-pyridinyl)aminomethylene]bis [phosphonic acid] tetraethyl ester 2-Amino-5-nitropyridine (10 g, 71.9 mmol), triethylorthoformate (11.7 g, 79.1 mmol) and diethylphosphite (21.86 g, 158.2 mmol) are heated at 140° C. in a round bottom flask fitted with a distillation head to collect ethanol throughout the course of the reaction. After heating 10 hours, the reaction mixture is cooled and then concentrated under reduced pressure. The desired product is obtained by flash chromatography with 5% isopropanol in methylene chloride on silica gel.

II. Synthesis of [(5-Amino-2-pyridinyl)aminomethylene]-bis[phosphonic acid] tetraethyl ester

[(5-Nitro-2-pyridinyl)aminomethylene]bis[phosphonic acid] tetraethyl ester (5.29 9, 12.4 mmol), absolute ethanol (100 ml) and 10% palladium on charcoal (1.3 g) are placed in a 500 ml Parr hydrogenation flask and hydrogenated for 4 hours at 40 psi. The reaction mixture is filtered through celite then concentrated under reduced pressure. The resultant solid is carried on without further purification.

III. Synthesis of [(5-Mercapto-2-pyridinyl) aminomethylene]bis[phosphonic acid] tetraethyl ester To nitrosonium tetrafluoroborate (NOBF$_4$) (22 mg, 0.19 mmol) in methylene chloride (6 ml) at room temperature is added [(5-amino-2-pyridinyl)aminomethylene]bis [phosphonic acid] tetraethyl ester (75 mg, 0.19 mmol). The reaction mixture is stirred 3 hours then concentrated under reduced pressure. The crude residue is dissolved in acetonitrile (6 ml) and sodium sulfide (46 mg, 0.19 mmol) is added. After stirring 12 hours at room temperature, the reaction is quenched by the addition of water and the mixture is extracted with methylene chloride. The organic extracts are combined and washed with 10% aqueous Na$_2$S$_2$O$_3$. The organic extracts are then dried over sodium sulfate, filtered and concentrated under reduced pressure. The desired thiol is obtained by flash chromatography purification with 2% isopropanol in methylene chloride.

IV. Synthesis of [(5-Mercapto-2-pyridinyl)aminomethylene] bis[phosphonic acid]

The bisphosphonic acid is obtained by refluxing the tetraethyl ester (0.5 mmol) in distilled water (25 ml) for 12 hours under an atmosphere of nitrogen. The reaction mixture is treated with charcoal, filtered and concentrated under reduced pressure. The crude residue is recrystallized from water and ethanol to provide [(5-mercapto-2-pyridinyl) aminomethylene]bis[phosphonic acid].

EXAMPLE D
Synthesis of [(4-(4-Mercaptobutyl)-2-pyridinyl) aminomethylene]bis[phosphonic acid]

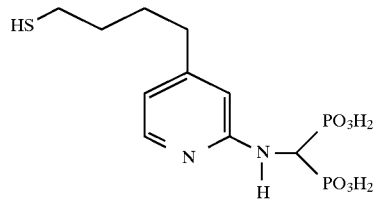

The compound above is prepared and synthesized as described hereinbelow.

I. Synthesis of [(4-Bromo-2-pyridinyl)aminomethylene]bis [phosphonic acid] tetraethyl ester Using essentially the same procedure as described in Example A (part I) hereinbefore, 2-amino-4-bromopyridine, triethylorthoformate and diethylphosphite are reacted to afford [(4-bromo-2-pyridinyl )aminomethylene]bis [phosphonic acid] tetraethyl ester.

II. Synthesis of [(4-(4-Hydroxybutyl-2-pyridinyl) aminomethylene]bis[phosphonic acid] tetraethyl ester To a solution of [(4-bromo-2-pyridinyl)aminomethylene] bis[phosphonic acid] tetraethyl ester(10 mmol) in THF (10 ml) cooled to −78° is added a solution of n-butyllithium (2.1 equivalent) in hexane over 30 minutes. The reaction is kept at −78° C. for an additional 30 minutes. To this solution is added 4-iodobutanol trimethylsilyl (TMS) ether (2.5 equivalent) and the reaction is allowed to warm to room temperature over 30 minutes. After standard aqueous workup, [(4-(4-butanol, TMS ether)-2-pyridinyl) aminomethylene]bis[phosphonic acid] tetraethyl ester is isolated and used in the next reaction without purification.

Cleavage of the TMS ether from the product is accomplished by stirring it in THF and adding a solution of tetrabutylammonuim fluoride (1M in THF) dropwise over 30 minutes. After a standard aqueous workup the resulting primary alcohol is isolated as an oil and used directly in the next reaction.

III. Synthesis of [(4-(4-Acetylthiobutyl)-2-pyridinyl) aminomethylene]bis[phosphonic acid] tetraethyl ester Using essentially the same sequence of reactions as described in Example A (part III and IV) hereinbefore, [(4-(4-hydroxybutyl)-2-pyridinyl)aminomethylene]bis [phosphonic acid] tetraethyl ester is converted to [(4-(4- acetylthiobutyl)-2-pyridinyl)aminomethylene]bis [phosphonic acid] tetraethyl ester.

IV. Synthesis of [(4-(4-Mercaptobutyl)-2-pyridinyl) aminomethylene]bis[phosphonic acid]

The thioacetate (5.0 mmol) is heated at reflux in 1N HCl (20 ml) for 8 hours. The reaction mixture is cooled, treated with charcoal, filtered and concentrated under reduced pressure. The desired product is obtained in suitable purity following trituration with acetone and further drying on a vacuum overnight.

EXAMPLE E
Synthesis of [(4-(4-Acetylthiobutyl)-2-pyridinyl) aminomethylene]bis[phosphonic acid]

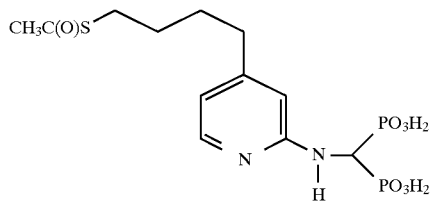

[(4-(4-Acetylthiobutyl)- 2-pyridinyl)aminomethylene]bis [phosphonic acid] is prepared by heating [(4-(4-acetylthiobutyl)-2-pyridinyl)-aminomethylene]bis [phosphonic acid] tetraethyl ester [prepared as described in Example D hereinbefore] at reflux in distilled water for 18 hours under an atmosphere of argon. The reaction mixture is concentrated under reduced pressure and the product is obtained by recrystallization from water and isopropanol.

EXAMPLE F
Synthesis of [[5-[(2-Mercapto-1-oxopropyl)amino]-2-pyridinyl]aminomethylene]bis[phosphonic acid]

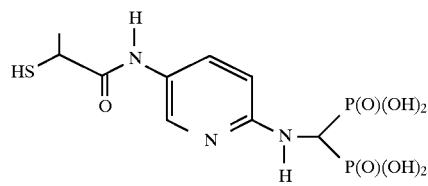

The above compound is prepared and synthesized as described hereinbelow.

I. Synthesis of [[5-[(2-Mercapto-1-oxopropyl)amino]-2-pyridinyl]aminomethylene]bis[phosphonic acid] tetraethyl ester Thiolactic acid (1.95 g, 18.38 mmol) is added slowly to the coupling agent, 1-(3-dimethylaminopropyl)-3-ethylcarbodiimide hydrochloride, (3.52 g, 18.38 mmol) in methylene chloride (15 ml) at 0° C. To this is then added [(5-amino-2-pyridinyl)aminomethylene]bis[phosphonic acid] tetraethyl ester [prepared as described in Example C (part II) hereinbefore] (4.84 g, 12.25 mmol) in methylene chloride (10 ml). The reaction mixture is stirred at room temperature under an atmosphere of nitrogen for 24 hours. The reaction mixture is diluted with methylene chloride (150 ml) then washed with water (2×150 ml) then with saturated aqueous NaCl (1×125 ml). The organic layer is dried over sodium sulfate, filtered and concentrated under reduced pressure. The amide is purified by flash chromatography on silica gel with 5% isopropanol in methylene chloride and obtained in a 52% yield as a yellow oil (3.05 g).

II. Synthesis of [[5-[(2-Mercapto-1-oxopropyl)amino]-2-pyridinyl]aminomethylene]bis[phosphonic acid]

The tetraethyl bisphosphonate (3.05 g, 6.31 mmol) is treated with bromotrimethylsilane (5.80 g, 37.89 mmol) in chloroform (25 ml) at room temperature under an atmosphere of nitrogen for 22 hours. The reaction mixture is quenched by the addition of methanol and then the reaction is concentrated under reduced pressure. The crude residue is triturated with ethyl acetate and further dried under high vacuum to provide the bisphosphonic acid (2.34 g) as a pale yellow solid in 100% yield.

EXAMPLE G
Synthesis of [2-Acetylthio-2-(3-pyridinyl)ethylidene]bis [phosphonic acid]

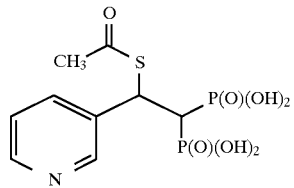

The above compound is prepared and synthesized as described hereinbelow.

I. Synthesis of 4,4'-(3-Pyridinylmethylene) bismorpholine

A suspension of benzene (10 ml) containing 3-pyridine carboxaldehyde (3.97 g, 37.09 mmol), boron trioxide (4.31 g, 61.94 mmol) and morpholine (7.76 g, 89.02 mmol) is stirred at room temperature for 2 hours. The reaction mixture is filtered through celite to remove the hydrated boron complex and the filtrate is concentrated under reduced pressure to provide a 73% yield of the bisaminal (7.17 g) in good purity.

II. Synthesis of [3-(2-Pyridinyl)ethenylidene]bis [phosphonic acid] tetraethyl ester To the bisaminal (1.00 g, 3.80 mmol) in toluene (6 ml) is added trifluoroacetic acid (0.89 g, 7.79 mmol). The mixture is heated for 15 minutes at 60° C., tetraethyl methylene diphosphonate (1.10 g, 3.80 mmol) is added and the reaction is stirred for a total of 22 hours at 60° C. The reaction mixture is cooled and water is added. The layers are separated and the aqueous layer is extracted with methylene chloride (3×15 ml). The organic layers are combined, dried over sodium sulfate, filtered and concentrated under reduced pressure. The bisphosphonate is separated from unreacted methylene diphosphonate and pyridine carboxaldehyde by flash chromatography on silica gel (97:3 methylene chloride/ isopropyl alcohol) to provide the vinyl adduct (296 mg) in 20% yield as a pale yellow oil.

III. Synthesis of [3-(2-Pyridinyl)ethenylidene]bis [phosphonic acid]

The bisphosphonate (1.66 g, 4.39 mmol) is treated with bromotrimethylsilane (5.38 g, 35.12 mmol) in chloroform at 50° C. for 12 hours under an atmosphere of nitrogen. The reaction mixture is then stirred for 30 minutes with water (20 ml) and ethyl acetate (20 ml). The layers are separated and the aqueous layer is treated with charcoal, filtered through celite and concentrated to provide the bisphosphonic acid (0.66 g) in 57% yield as a pale yellow solid.

IV. Synthesis of [2-Acetylthio-2-(3-pyridinyl)ethylidene]bis [phosphonic acid]

To [3-(2-pyridinyl)ethenylidene]bis[phosphonic acid] (0.56 g, 2.11 mmol) in water (5 ml) is added thioacetic acid (0.80 g, 10.55 mmol). After stirring at room temperature for 5 hours, the reaction mixture is concentrated under reduced pressure, triturated with acetone and then dried under high vacuum to provide the bisphosphonic acid as a pale yellow solid (375 mg) in 52% yield.

EXAMPLE H
Synthesis of [2-Mercapto-2-(3-pyridinyl)ethylidene]bis[phosphonic acid]

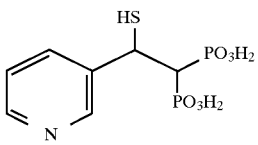

The compound above is prepared and synthesized as described hereinbelow.

I. Synthesis of [2-Acetylthio-2-(3-pyridinyl)ethylidene]bis[phosphonic acid] tetraethyl ester

[3-(2-Pyridinyl)ethenylidene]bis[phosphonic acid] tetraethyl ester (1.0 g, 2.65 mmol) [prepared as described in Example G (part II) hereinbefore] and thioacetic acid (0.30 g, 3.98 mmol) are stirred in anhydrous chloroform (15 ml) for 48 hours at room temperature. The reaction mixture is then concentrated under reduced pressure. The residue is dissolved in acetone and concentrated a second time under vacuum to provide the thioacetate (1.01 g) in an 83% yield.

II. Synthesis of [2-Mercapto-2-(3-pyridinyl)ethylidene]bis[phosphonic acid]

The bisphosphonic acid is prepared by heating [2-acetylthio-2-(3-pyridinyl)ethylidene]bis[phosphonic acid] tetraethyl ester (1.01 g, 2.21 mmol) at reflux in concentrated hydrochloric acid for 3 hours. The solution is then evaporated to dryness under reduced pressure. The crude residue is dissolved in warm water and treated with charcoal and then filtered through celite. The aqueous filtrate is extracted with methylene chloride twice. The product is precipitated from the aqueous filtrate by the addition of ethanol. The precipitate is collected by filtration, washed with diethyl ether and vacuum dried in a desiccator.

EXAMPLE I
Synthesis of [5-Mercapto-2-(3-pyridinyl)pentylidene]bis[phosphonic acid]

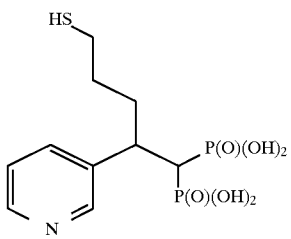

The compound above is prepared and synthesized as described hereinbelow.

I. Synthesis of 5-hydroxy-2-(3-pyridinyl)pentanoic acid ethyl ester, tert-butyldimethylsilyl ether To a solution of ethyl 3-pyridyl acetate (0.76 g, 4.60 mmol) in anhydrous THF (125 ml) at −78° C. under an atmosphere of argon is added lithium diisopropyl amide (4.60 mmol) in THF (25 ml). The solution is allowed to stir 30 minutes at −78° C. and then to this solution is added 3-iodopropanol, tert-butyldimethylsilyl ether (5.00 mmol) in THF (20 ml). The reaction is stirred at −78° C. an additional two hours and then at room temperature for 8 hours. The reaction mixture is quenched by the addition of a solution of saturated aqueous ammonium chloride. The layers are separated and the aqueous layer is extracted with diethyl ether. The organic layers are combined, dried and then concentrated under reduced pressure. The product is purified by flash chromatography with 20% methylene chloride in hexanes on silica gel.

II. Synthesis of 2-(3-pyridinyl)pentan-1,5-diol, 5-tert-butyldimethylsilyl ether The carboxylate (2.25 mmol) is reduced to the corresponding alcohol by treatment with lithium aluminum hydride (5.50 mmol) in refluxing THF (100 ml) under an atmosphere of nitrogen. The reaction is quenched by the careful addition water followed by treatment of the aluminum salts with dilute aqueous NaOH. The reaction mixture is filtered through celite and then the layers are separated and the aqueous layer is extracted with diethyl ether. The organic layers are combined, dried and concentrated under reduced pressure. The resulting oil is used without further purification.

III. Synthesis of 5-bromo-4-(3-pyridinyl)pentanol, tert-butyldimethylsilyl ether A mixture of 2-(3-pyridinyl)pentan-1,5-diol, 5-tert-butyldimethylsilyl ether (10 mmol), carbon tetrabromide (11 mmol) and triphenyl phosphine (11 mmol) in dichloromethane (100 ml) is stirred at room temperature for 5 hours. Water is added and the product is extracted with dichloromethane. The combined organic extracts are dried and concentrated. The residue is purified by flash column chromatography to give 5-bromo-4-(3-yridinyl)pentanol, tert-butyldimethylsilyl ether.

IV. Synthesis of 5-hydroxy-2-(3-pyridinyl)pentylphosphonic acid, diethyl ester, tert-butyldimethylsilyl ether A solution of 5-bromo-4-(3-pyridinyl)pentanol, tert-butyldimethylsilyl ether (0.75 mol) and triethyl phosphite (1.12 mmol) is heated at 90° C. for 72 hours while maintaining a flow of nitrogen through the reaction. The excess trimethyl phosphate is removed by distillation and the crude residue is chromatographed with 2% isopropanol in methylene chloride on silica gel. The product can be used in the following reaction without further purification.

V. Synthesis of [5-hydroxy-2-(3-pyridinyl)pentylidene]bis[phosphonic acid] diethyl ester, tert-butyldimethylsilyl ether To a solution of 5-hydroxy-2-(3-pyridinyl)pentylphosphonic acid, diethyl ester, tert-butyldimethylsilyl ether(15.0 mmol) in anhydrous THF (200 ml) is added sec-butyllithium (33.0 mmol, 1.3M in cyclohexane) at 0° C. Following the addition, stirring is continued for an additional 30 minutes. This solution is then slowly added to a solution of diethyl chlorophosphate (2.50 g, 14.47 mmol) in anhydrous THF (100 ml) at room temperature. After stirring the reaction overnight, the mixture is quenched by the addition of a saturated aqueous solution of sodium bicarbonate and then extracted with methylene chloride. The combined organic extracts are dried over anhydrous sodium sulfate, filtered and concentrated under reduced pressure. The crude product is purified by flash chromatography with 30% acetone in hexanes on silica gel.

VI. Synthesis of [5-hydroxy-2-(3-pyridinyl)pentylidene]bis[phosphonic acid] diethyl ester The silyl ether is cleaved by treatment of the ether (0.50 mmol) in THF at room temperature with tetrabutyl ammonium fluoride (0.75 mol) for 30 minutes. After deprotection is complete, the reaction mixture is washed with a saturated solution of NaCl. The organic layer is dried over sodium sulfate, filtered and then concentrated under reduced pressure. The resulting residue is used without further purification.

VII. Synthesis of [5-bromo-2-(3-pyridinyl)pentylidene]bis[phosphonic acid] diethyl ester Using essentially the same conditions as described in part III hereinbefore, [5-hydroxy-2-(3-pyridinyl)pentylidene]bis

[phosphonic acid] diethyl ester is converted to [5-bromo-2-(3-pyridinyl)pentylidene]bis [phosphonic acid] diethyl ester.

VIII. Synthesis of [5-acetylthio-2-(3-pyridinyl)pentylidene] bis [phosphonic acid] diethyl ester A solution of [5-bromo-2-(3-pyridinyl)pentylidene]bis [phosphonic acid] diethyl ester (5.0 mmol) is stirred in dry acetone (35 ml) and sodium thioacetate (5.2 mmol) is added. The mixture is stirred at 50° C. for 12 hours. After cooling to room temperature the solvent is removed under reduced pressure. The crude residue is dissolved in methylene chloride and washed with water. The organic layer is then dried and concentrated under reduced pressure. The desired product is purified by flash chromatography using a 5–10% isopropanol in methylene chloride gradient on silica gel.

IX. Synthesis of [5-mercapto-2-(3-pyridinyl)pentylidene]bis [phosphonic acid]

[5-Acetylthio-2-(3-pyridinyl)pentylidene]bis [phosphonic acid] diethyl ester (4.2 mmol) is dissolved in 2.5M HCl (65 ml) and is heated to reflux for 7 hours. The reaction mixture is cooled and concentrated under reduced pressure. The solid residue is triturated with acetone and then recrystallized from water and ethanol yielding 5-mercapto-2-(3-pyridinyl)pentylidene]bis [phosphonic acid].

EXAMPLE J

Schenk Model

The compounds are evaluated for in vivo bone resorption inhibition and mineralization inhibition in an animal model system known in the field of bone metabolism as the Schenk Model. The general principles of this model system are disclosed in Shinoda et al., *Calcif. Tissue Int.*, 35, 87–99 (1983); and in Schenk et al., *Calcif. Tissue Res.* 11, 196–214 (1973), the disclosures of which are incorporated herein by reference.

Materials and Methods

Animals

Preweaning 17-day-old (30 gms) male Sprague Dawley rats (Charles River Breeding Laboratories) are shipped with their mothers and placed in plastic cages with their mothers upon arrival. At 19 days of age, pups receiving Rat Chow and water ad libitum are randomly allocated into treatment or control groups comprising seven animals per group. On day 1 and again on day 7 all animals are given an intraperitoneal ("IP") injection of Calcein (1% solution in 0.9% saline solution; dosed at 0.2 ml/100 g body weight). On day 4 all animals are given an IP injection of tetracycline hydrochloride (1% solution in 0.9% saline solution; dosed at 0.2 ml/100 g body weight). These compounds label actively mineralizing bone and cartilage.

Dose Solutions and Dosing Procedure

All solutions are prepared for subcutaneous injection in 0.9% normal saline and adjusted to pH 7.4 using NAOH and/or HCl. Dose solution calculation is made by considering the mass of powder (based on molecular weight, hydration) of the active material in mg/kg (body weight) that corresponds to mgp/kg. Concentrations are based on dosing 0.2 ml/100 g body weight. Typically, all compounds are administered at 0.01, 0.1, 1.0 and 10.0 mg P/kg/day for 7 days. Compounds showing activity at 0.1 mg P/kg/day are then tested at logarithmic decrements down to 0.001 mg P/kg/day. Adjustments in dosage based on changes in body weight are made on a daily basis.

Necropsy, Tissue Processing and Histomorphometry

On day 8 after the start of dosing, all animals are sacrificed by IP overdose of pentabarbitol. Tibias are dissected free and placed in 70% ethyl alcohol. One tibia is dehydrated in graded ethanol solutions and embedded in methyl methacrylate as described in Schenk, *Methods of Calcified Tissue Preparation* (G. R. Dickson, Editor; Elsevier Science Publ., The Netherlands; 1984), the disclosures of which are incorporated herein by reference in their entirety. The tibia is sectioned longitudinally through the metaphyseal area. Specimens are stained on one surface with silver nitrate and mounted on microscope slides for evaluation with a Quantimet Image Analyzer (Cambridge Instruments, Inc.) using both incandescent and ultraviolet illumination. Metaphyseal trabecular bone content is measured in the region between the fluorescent label and the growth plate: expressed as percent of total area (bone+marrow). Epiphyseal growth plate width is obtained as the mean value of 10 equally-spaced measurements across the section.

Statistical evaluation of data is made using parametric and non-parametric analysis of variance and Wilcoxons rank sum test to determine a statistically significant effect compared to control animals.

The Schenk model provides data for in vivo bone resorption inhibition by the compounds. The lowest effective (antiresorptive) dose ("LED") for representative compounds tested, as determined by the Schenk model, are provided in Table 2.

EXAMPLE K

Adjuvant Arthritis Model

There are numerous animal models of arthritis, among these is adjuvant-induced arthritis using *Mycobacterium butyricum*. This model in a number of ways mimics rheumatoid arthritis in the human (joint swelling associated with cellular and pannus invasion of the joint space, bone resorption, and release of chemotaxic factors and lysosomal constituents into the joint space) (1,2). A number of prophylactic and therapeutic studies have indicated the potential use of anti-inflammatory drugs (3,4) and diphosphonates in arthritis (5,6).

REFERENCES

1. Pearson, C., Wood F. (1959), Studies of Polyarthritis and Other Lesions Induced by Injection of Mycobacterial Adjuvant. 1. General Clinical and Pathological Characteristics and Some Modifying Factors, *Arth. Rheum.*, 2:440–459.
2. Blackman, A., Burns, J. W., Framer, J. B., Radziwonik, H., Westwick, J. (1977), An X-ray Analysis of Adjuvant Arthritis in the Rat. The Effect of Prednisolone and Indomethacin, *Agents and Actions*, 7:145–151.
3. Winter, C. A., Nuss, G. W. (1966), Treatment of Adjuvant Arthritis in Rats with Anti-inflammatory Drugs, *Arth. Rheum.*, 9:394–404.
4. Winder, C. V., Lembke, L. A., Stephens, M. D. (1969), Comparative Bioassay of Drugs in Adjuvant-Induced Arthritis in Rats: Flufenamic Acid, Mefenamic Acid, and Phenylbutazone, *Arth. Rheum.*, 12:472–482.
5. Francis, M. D., Flora, L. King, W. R. (1972), The Effects of Disodium Ethane-1-Hydroxy-1-Diphosphonate on Adjuvant Induced Arthritis in Rats, *Calcif. Tiss. Res.*, 9:109–121.
6. Flora, L. (1979), Comparative Antiinflammatory and Bone Protective Effects of Two Diphosphonates in Adjuvant Arthritis, *Arth. Rheum*, 22:340–346.

Adjuvant arthritis is a severe cellulitis and synovitis induced in male rats (either Sprague Dawley or Lewis strain) by a single subcutaneous (SC) injection of *Mycobacterium butyricum* (8 mg/ml) in mineral oil on day 0. The compounds are dosed once daily either orally (PO) or parenterally (SC) and can be tested in either prophylactic (from day 0) or therapeutic (from day 9 or 10 or 14) protocols. Antiarthritic efficacy can be measured as a reduction in paw volume, body weight loss, bone loss or reactive new bone formation compared to the saline-treated arthritic controls. Treatment can be stopped and the "flare" response (rapid increase in inflammation) examined, which indicates a compound's ability to maintain efficacy.

Materials and Methods

A. Animals

Animals used are male Lewis rats (LEW). On arrival, the rats are randomized by computer generated random numbers and placed in individual wire suspended cages. Food and water are administered ad libitum, throughout the entire study. Routine care and maintenance of the animals are performed according to State and Federal regulations. Each rat is identified with a number placed in front of the cage and on the tail of the rat.

B. Experimental Design

On day 1 body weights (BW) and hind paw volume [(PV) recorded by a mercury displacement method using a pressure transducer linked into a computer] measurements are taken on all rats. On day 0, the induction of arthritis using MFA [*Mycobacterium butyricum* (Mb) 4.4 mg/kg in oil] is as follows: rats are anesthetized and receive a single SC injection of MFA at the base of the tail under aseptic conditions.

Paw volumes and body weights are measured thereafter on various days, usually twice a week. For the prophylactic protocol, rats are randomly allocated into groups of 8–10 rats and treatment begins on day 0 and continues daily until termination. For the therapeutic protocol, the rats are randomized into treatment groups of 8–10 rats according to their PV on day 10. Dosing begins on day 10 and continues daily until termination. For both protocols, animals are placed in shoe box cages with deep bedding on or before day 10.

Dosing Solutions For Compounds Unlikely to Oxidize

Drugs are weighed out on a calibrated balance and then mixed with distilled water in a volumetric flask. The solution is adjusted to pH 7.4 with 0.1N NaOH. Then the solution is filtered through a 0.45 μm sterile filter into a sterile storage container. When not in use, the solution is stored in the refrigerator.

For Compounds Likely to Oxidize

Drugs are weighed out on a calibrated balance and then mixed with deoxygenated water in a volumetric flask. The stock solution is filtered through a 0.45 μm sterile filter into a sterile storage container. When not in use, the stock solution is kept refrigerated.

On a daily basis, a specific amount of solution is removed from the stock solution, put into small dosing beaker and then adjusted to pH 7.4 according to a predetermined calculation. Further dilutions of the adjusted solution can be made if necessary (with deoxygenated water).

Drug calculations are made based on the molecular weight, the purity of the compound, the amount based on mg/kg (body weight) and the desired final concentration in mgP/kg. The volume dosed per rat is 0.1 ml/100 gm of body weight sub-cutaneously, given as an injection in the inguinal fold of the animal, alternating sides each day or 1 ml/200 gm BW given orally using a curved stainless steel dosing tube. Adjustments based on changes in body weight are made weekly.

Radiographs, Necropsy and Tissue Collection

At termination, each rat is sacrificed with 1 ml Socomb® intraperitoneally (IP). Immediately a whole body radiograph is taken by a Torrox 120D x-ray unit at MA=5, ISUP=50 and time=60 sec. on Kodak non-screen medical film. Hind legs are removed from each rat and fixed in 10% buffered formalin along with a piece of liver, kidney, spleen, and thimus. The tibiotarsal joints are decalcified in 4% EDTA, pH 7.4 and processed routinely in paraffin blocks and H+E stain. The organ parts also processed in paraffin and stained H+E.

The histology sections are evaluated qualitatively for bone and soft tissue lesions using light microscopy. Radiographs are graded for bone resorption (BR) in 6 anatomical trabecular bone sites in each hind leg and 4 sites in each front leg on a scale of 0–3 giving an arbitrary score of 0–60 for all 4 legs. For reactive new bone formation (RNB), radiographs are graded on a severity scale of 0–3 for the lateral and medical surfaces of the tibia and then 0–2 for all other areas mentioned above, giving an arbitrary score of 0–44.

D. Statistical Analysis

Data analysis on paw volume, bone resorption and reactive new bone formation is performed by student's t-test and one-way analysis of variance with Tukeys (SAS) (12). Differences are considered significant at p=0.05 or less.

This model provides in vivo data for the efficacy of antiarthritic compounds in terms of reducing paw swelling bone loss and reactive new bone formation compared to the saline treated arthritic animals.

EXAMPLE L

Capsules are prepared by conventional methods, comprised as follows:

| Active Ingredient | Mg Per Capsule |
|---|---|
| [5-Mercapto-2-(3-pyridinyl) pentylidene bis[phosphonic acid] Excipients | 350.0 |
| Lactose | 90.0 |
| Microcrystalline Cellulose | 60.0 |
| Magnesium Stearate | 1.0 |

The capsules having the above composition are prepared using conventional methods as described below:

The active ingredient is mixed with the microcrystalline cellulose in a turn shell blender for approximately ten (10) minutes.

The resulting mixture is passed through a hammer mill with an 80 mesh screen.

The mixture is put back into the twin shell blender along with the lactose and is then mixed for approximately fifteen (15) minutes.

The magnesium stearate is next added and blended for an additional five (5) minutes. The resulting blend is then compressed on a piston-activated capsule filler.

EXAMPLE M

Tablets are prepared having the following composition:

| Active Ingredient | Mg Per Tablet |
|---|---|
| [2-Mercapto-2-(3-pyridinyl) ethylidene]bis[phosphonic acid] | 700.0 |
| Excipients | |
| Lactose (spray-dried) | 200.0 |
| Starch (1500) | 100.0 |
| Magnesium Stearate | 25.0 |

Tablets are prepared having the above composition using conventional methods as described below:

The active ingredient is ground in a ball mill for approximately thirty (30) minutes. The milled active ingredient is then blended in a twinblade mixer with the spray-dried lactose for approximately twenty (20) minutes.

The starch is added to the mixture and is then mixed for an additional fifteen (15) minutes. The blend is compressed into tablets on a standard tablet press.

The above tablets administered orally twice daily for 6 months substantially reduce bone resorption in a patient weighing approximately 70 kilograms afflicted with Paget's disease. Similar results are obtained when [2-Mercapto-2-(3-pyridinyl) ethylidene]bis[phosphonic acid] in the above described tablets is replaced with [(5-(3-Mercaptopropyl)-2-pyridinyl)aminomethylene]bis[phosphonic acid]; [(5-(3-Acetylthiopropyl)-2-pyridinyl)aminomethylene]bis[phosphonic acid]; [(5-Mercapto-2-pyridinyl)aminomethylene]bis[phosphonic acid]; [(4-(4-Acetylthiobutyl)-2-pyridinyl)aminomethylene]bis[phosphonic acid]; [(4-4-Mercaptobutyl)-2-pyridinyl)aminomethylene]bis[phosphonic acid; or a pharmaceutically acceptable salt or ester of these diphosphonate compounds.

EXAMPLE N

Injectable solutions are prepared by conventional methods using 10.0 ml of physiological saline solution and 7.0 mg P of [2-mercapto-2-(3-pyridinyl)ethylidene]bis[phosphonic acid] adjusted to pH=7.4.

One injection, one time daily for 4 days, results in appreciable alleviation of hypercalcemia of malignancy in patients weighing approximately 70 kilograms.

EXAMPLE O

A Caucasian male, weighing approximately 92 kilograms, seventy-two years of age, suffering from moderate to severe pain, and occasional swelling, of the right knee. After approximately one year of steadily increasing discomfort, he visits a physician who renders a clinical diagnosis of osteoarthritis of the right knee, which was subsequently verified by X-ray diagnosis.

After a period of ameliorative therapy of various NSAIDs, including aspirin, naprosen, and ketoprofen, his symptoms continue to worsen and his condition appears to degenerate. He returns to his physician who then prescribes the tablets prepared as described in Example M twice daily two hours before or after meals for a period of three months. His clinical symptoms of pain and swelling, particularly with extended walking, improved significantly after his 3 months of therapy. At the conclusion of three months at a dosage of 1 capsule prepared as described in Example R per day, the therapy is continued at one-half the dosage originally prescribed (i.e. 1 capsule per day) indefinitely.

EXAMPLE P

A black female, weighing approximately 65 kilograms, fifty-five years of age, presents with swelling and deformation of the finger joints of both hands, with partial loss of strength and/or dexterity of her fingers and hands. Upon visual and X-ray examination and various appropriate clinical tests approved by the American Rheumatological Association (ARA) she is diagnosed with rheumatoid arthritis.

After an unsuccessful analgesic and anti-inflammatory therapy, her physician prescribes the tablets prepared in Example M, two times daily two hours before or after meals for a period of four months. After a month of therapy, her symptoms of knuckle swelling noticeably improves and her range of finger motion increases significantly; she continues therapy for the remainder of the four months, after which her physician continues the prescribed dose for an additional two months.

EXAMPLE Q

A female of Hispanic origin, twelve years of age, weighing approximately 37 kilograms, presents to the physician with idiopathic juvenile rheumatoid arthritis. Her symptoms include marked inflammation of multiple joints, complicated by heat and tenderness and indicating rapid and pathological degeneration of joint function.

Her physician refers her to a rheumatologist who immediately prescribes aggressive therapy by IV administration of the solution prepared as described in Example N over a period of three days, at the rate of 1 injection per day, administered over two hours. At the conclusion of the IV regimen, the physician prescribes the two tablets prepared as described in Example M, twice a day, two hours before or after meals, for a period of two months, during which she exhibits marked improvement with increased mobility and decreased pain. For the succeeding two months, the physician reduces her dose to ¾ of the original oral dose by prescribing 3 tablets over a period of two days, i.e. one 2-capsule day alternating with one 1-capsule day. At the conclusion of this regimen the dosage is again reduced to ¼ of the original oral dose by giving her the capsules prepared as described in Example L, 1 capsule every day for an additional four months.

What is claimed is:

1. A thio-substituted, nitrogen-containing heterocyclic phosphonate compound, or a pharmaceutically-acceptable phosphonic acid salt or ester thereof, having the following structure:

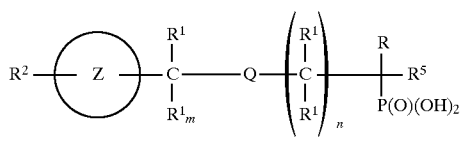

wherein m and n are integers 0 to 10 and m+n equals 0 to 10;

(a) Z is a monocyclic heterocyclic ring moiety containing one or more heteroatoms selected from O, S, or N, at least one of which is N;

(b) Q is covalent bond, S, O, N, or $NR^1$;

(c) R is $PO_3H_2$ or $P(O)(OH)R^4$, wherein $R^4$ is a substituted or unsubstituted $C_1$–$C_8$ alkyl;

(d) each $R^1$ is independently selected from —$SR^6$; —$R^8SR^6$; nil; hydrogen; unsubstituted or substituted $C_1$–$C_8$ alkyl; unsubstituted or substituted aryl; hydroxy; —$CO_2R^3$; —$O_2CR^3$; —$NR^3_2$; —$OR^3$; —$N(R^3)C(O)R^3$; —$C(O)N(R^3)_2$; substituted or unsubstituted benzyl; nitro; or combinations thereof;

(e) $R^2$ is a substituent on atoms in the Z moiety and is independently selected from —$SR^6$; —$R^8SR^6$; —$CO_2R^3$; —$O_2CR^3$; —$NR^3_2$; —$N(R^3)C(O)R^3$; —$OR^3$; —$C(O)N(R^3)_2$; nil; hydrogen; unsubstituted or substituted $C_1$–$C_8$ alkyl; unsubstituted or substituted aryl; hydroxy; substituted or unsubstituted benzyl; nitro; or combinations thereof;

(f) each $R^3$ is independently selected from hydrogen; substituted or unsubstituted $C_1$–$C_8$ alkyl; or —$R^8SR^6$;

(g) $R^5$ is selected from —$SR^6$; —$R^8SR^6$; hydrogen; hydroxy; amino; halogen; unsubstituted or substituted $C_1$–$C_8$ alkyl; and (h) $R^6$ is H, —$C(O)R^7$; —$C(S)R^7$; —$C(O)N(R^7)_2$; —$C(S)N(R^7)_2$; —$C(O)OR^7$ or —$C(S)OR^7$; where $R^7$ is hydrogen, or unsubstituted or substituted $C_1$–$C_8$ alkyl;

(i) $R^8$ is substituted or unsubstituted $C_1$–$C_8$ alkyl; and at least one of $R^1$, $R^2$, $R^3$, $R^4$, or $R^5$ must be —$SR^6$ or —$R^8SR^6$.

2. A compound, according to claim 1, wherein Z is a monocyclic heterocyclic ring moiety.

3. A compound, according to claim 2, wherein Z is a six-membered heterocylcic ring.

4. A compound, according to claim 3, wherein Z is pyridine, pyrimidine, piperadine, and dihydropyridine.

5. A compound, according to claim 4, wherein Z is pyridine.

6. A compound, according to claim 2, wherein Z is a five-membered heterocyclic ring.

7. A compound, according to claim 6, wherein Z is imidazole, thiazole, oxazole, pyrrole, furan, thiophene, or pyrrolidine.

8. A compound, according to claim 1, wherein Q is N or $NR^1$.

9. A compound, according to claim 1, wherein $R^1$ is independently selected from —$SR^6$; $R^8SR^6$; hydrogen; substituted or unsubstituted $C_1$–$C_8$ alkyl; —$NR^3_2$; or —$CO_2R^3$.

10. A compound, according to claim 9, wherein $R^1$ is —$SR^6$, $R^8SR^6$, or hydrogen.

11. A compound, according to claim 1, wherein $R^2$ is —$SR^6$; $R^8SR^6$; hydrogen; substituted or unsubstituted $C_1$–$C_8$ alkyl; —$NR^3_2$; or —$CO_2R^3$.

12. A compound, according to claim 11, wherein $R^2$ is —$SR^6$; $R^8SR^6$; or hydrogen.

13. A compound, according to claim 1, wherein $R^3$ is hydrogen or $R^8SR^6$.

14. A compound, according to claim 9, wherein $R^3$ is hydrogen or $R^8SR^6$.

15. A compound, according to claim 1, wherein $R^3$ is hydrogen or $R^8SR^6$.

16. A compound, according to claim 9, wherein $R^6$ is H; —$C(O)R^7$; $C(S)R^7$; or $C(O)N(R^7)_2$.

17. A compound, according to claim 16, wherein $R^6$ is H; —$C(O)R^7$; or $C(S)R^7$.

18. A compound, according to claim 16, wherein $R^6$ is H; —$C(O)R^7$; $C(S)R^7$; or $C(O)N(R^7)_2$.

19. A compound, according to claim 16, wherein $R^6$ is H; —$C(O)R^7$; $C(S)R^7$; or $C(O)N(R^7)_2$.

20. A compound, according to claim 11, wherein $R^6$ is H; —$C(O)R^7$; $C(S)R^7$; or $C(O)N(R^7)_2$.

21. A pharmaceutical composition comprised of a safe and effective amount of a compound according to claim 1 and pharmaceutically acceptable excipients.

22. A composition according to claim 21 comprised of 0.1% to 99.9% by weight of the compound according to claim 1.

23. A composition according to claim 22 comprised of 20% to 80% by weight of the compounds of the present invention.

24. A composition according to claim 22 comprised of 15% to 95% of a compound according to claim 1; 0–2% flavoring agents; 0–50% co-solvents; 0–5% buffer system 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

25. A method of treating or preventing disorders associated with abnormal calcium and phosphate metabolism wherein a safe and effective amount of a compound according to claim 1 is administered to a human or other mammal in need of such treatment.

26. A method according to claim 25 wherein said human or other mammal is suffering from osteoporosis.

27. A method according to claim 25 wherein said human or other mammal is suffering from arthritis.

28. A method according to claim 25 wherein said human or other mammal is suffering from osteoarthritis.

29. A method according to claim 26 wherein said human or other mammal is suffering from rheumatoid arthritis.

30. A method of treating or preventing disorders associated with abnormal calcium and phosphate metabolism wherein a human or other mammal in need of such treatment is administered a pharmaceutical composition according to claim 22.

* * * * *